US006989396B2

(12) United States Patent
Kinghorn et al.

(10) Patent No.: US 6,989,396 B2
(45) Date of Patent: Jan. 24, 2006

(54) **TROPANE ALKALOID MULTIDRUG RESISTANCE INHIBITORS FROM *ERYTHROXYLUM PERVILLEI* AND USE OF THE SAME**

(75) Inventors: A. Douglas Kinghorn, Chicago, IL (US); John M. Pezzuto, River Forest, IL (US); Baoliang Cui, Palisades Park, NJ (US); Gloria L. Silva, Cordoba (AR); Min You, Indianapolis, IN (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 273 days.

(21) Appl. No.: 10/119,874

(22) Filed: Apr. 10, 2002

(65) Prior Publication Data

US 2003/0092729 A1    May 15, 2003

Related U.S. Application Data

(60) Provisional application No. 60/283,394, filed on Apr. 12, 2001.

(51) Int. Cl.
*A61K 31/46* (2006.01)
*C07D 451/04* (2006.01)

(52) U.S. Cl. .................. 514/350; 546/124; 514/350
(58) Field of Classification Search ................ 514/350; 546/124
See application file for complete search history.

(56) References Cited

FOREIGN PATENT DOCUMENTS

EP         0 787 716 A1    8/1997
WO        WO 97/01336      1/1997

OTHER PUBLICATIONS

Glaser, Robert et al. "Stereochemistry of the N-methyl Group in Salts of Tropane Alkaloids," J. Org. Chem. (1998), vol. 53, pp 2172-2180.*
Chavez et al., *J. Nat. Prod.*, 65, 606-610, (2002).
Silva et al., *J. Nat. Prod*, 64, 1514-1520, (2001).
Mi et al., *Cancer Research*, 61, 4030-4037, (2001).
M.M. Gottesman et al., *Ann. Rev. Biochem.*, 62: 385-427, (1993).
M. Horio et al., *Biochem. Biophys. Acta*, 1061:106-110, (1991).
W.V.D. Vrie et al., *Crit. Rev. Clin. Lab. Sci.*, 35:1-57, (1998).
A.H. Dantzig et al., *Cancer Res.*, 56:4171-4179, (1996).
J.M. Ford et al., *Pharmacol. Rev.*, 42: 155-199, (1990).
T. Watanabe et al., *Acta Oncol.*, 34:235-241, (1995).
H.L. Pearce et al., *Proc. Natl. Acad. Sci. USA*, 86:5128-5132, (1989).
H. Echizen et al., *Am. Heart J.*, 109:210-217, (1985).
M. Naito et al., *Cancer Chemother. Pharmacol.*, 40:S20-S24, (1997).

F. Bichat et al., *Biochem. Pharmacol.*, 56:497-502, (1998).
F. Hyafil et al., *Cancer Res.*, 53: 4595-4602, (1993).
T. Tsuruo et al., *Cancer Res.*, 43: 2905-2910, (1983).
T. Tsuruo et al., *Cancer Treat. Rep.*, 69:523-525, (1985).
H. Shinoda et al., *Cancer Res.*, 49:1722-1726, (1989).
A. Kiue et al., *Br. J. Cancer;* 64:221-226, (1991).
L. Kraus-Berthier et al., *Acta Oncol.*, 33:631-637, (1994).
W.T. Bellamy et al., *Cancer Invest.*, 8:547-562, (1990).
G.D. Pennock et al., *J. Natl. Cancer Inst.*, 83:105-110, (1991).
K. Ueda et al., *Anti-Cancer Drug Des.*, 14:115-121 (1999).
M.J. Newman et al., *Cancer Res.*, 2964-72, (2000).
M. You et al., *J. Nat. Prod.*, 57:1517-1522, (1994).
M. You et al., *J. Nat. Prod.*, 58:598-604, (1995).
G.L. Silva et al., *J. Nat. Prod.*, 64, pp. 1514-1520 (2001).
J.J. Casciari et al., *J. Natl. Cancer Inst.*, 86:1846-1852, (1994).
M.G. Hollingshead et al., *Life Sci.*, 57:131-141, (1995).
W.T. Beck et al., *Cancer Res.*, 39:2070-2079, (1979).
W.T. Beck et al., *Cancer Res.*, 46:778-784, (1986).
M.M. Cornwell et al., *J. Biol Chem.*, 281: 7921-7928, (1986).
A. Somanabandhu et al., *J. Nat. Prod.*, 56:233-239, (1993).
L.L. Song et al., *Cancer Res.*, 59:578-585, (1999).
A. Fojo et al., *Cancer Res.*, 45:3002-7, (1985).
L. Wu et al., *Cancer Res.*, 52:3029-3034, (1992).
V. Gekeler et al., *Biochem. Biophys. Res. Commun.*, 206: 119-126, (1995).
D.P. Waller et al., *Contraception*, 22:183-187, (1980).
D. Shen et al., *J. Biol. Chem.*, 261:7762-7770, (1986).
K.N. Thimmaraih et al., *Oncol. Res.*, 10: 29-41, (1998).
C. Muller et al., *Int. J. Cancer,* 56: 749-754, (1994).
K.E. Sampson et al., *Cancer Lett.*, 68:7-14, (1993).
Y.P. Hu et al., *Anti-Cancer Drugs*, 7:738-744, (1996).
M.M. Cornwell et al., *J. Biol. Chem.*, 262:2166-2170, (1987).
C. Pascuad et al., *Biochem. J.*, 333:351-358, (1998).
W.D. Stein, *Physiol. Rev.* 77:545-590, (1997).
G. Klopman et al., *Mol. Pharmacol.*, 52:323-334, (1997).

(Continued)

*Primary Examiner*—Kamal A. Saeed
*Assistant Examiner*—Janet L Coppins
(74) *Attorney, Agent, or Firm*—Marshall, Gerstein & Borun LLP

(57) ABSTRACT

Compounds and methods of modulating the activity of P-glycoproteins are disclosed. The method utilizes compounds derived from *Erythroxylum pervillei*. The compounds overcome multidrug resistance and can be used therapeutically to enhance performance of therapeutic drugs, like chemotherapeutic drugs and antibiotics.

3 Claims, 4 Drawing Sheets

OTHER PUBLICATIONS

J.M. Zamora et al., *Mol. Pharmacol.,* 33:454-462, (1988).
J.L. Weaver et al., *Int. J. Cancer,* 54:456-461, (1993).
G. Klopman et al., *Cancer Res.,* 52:4121-4129, (1992).
R.M. Phillipes et al., *Cancer Res.,* 58:5263-5266, (1998).
M.S. Al-Said et al., *Phytochemistry,* 25, 851-853, (1986).
C.G. Chaves et al., C.G.; Schapoval, E.E.S.; Zuanazzi, J.A.; Diehl, E.; de Siqueira, N.C.S.; Henriques, A.T., *Erythoxylum argentinum*: Assays for Anti-inflammatory Activity., *J. Ethnopharmacol.,* 22, 117-120, (1988).
K. Doerk-Schmitz et al., *Phytochemistry,* 35, 107-110 (1994).
G. Fodor et al., *Nat. Prod. Rep.,* 11, 443-450, (1994).
R. Glaser et al., *J. Org. Chem.,* 53, 2172-2180 (1988).
M.S. Al-Said et al., *J. Chem. Soc., Perkin Trans., 1*: 957-959, (1986).
J.T. Agar et al., *J. Chem. Soc., Perkin Trans., 1*: 1550-1553, (1976).
A.L. Payo-Hill et al., *Phytochemistry,* 54, 927-932, (2000).
T.A. Broadbent et al., *Heterocycles,* 20, 863-980, (1983).
G.A. Cordell et al., *Tetrahedron,* 47, 3521-3534, (1991).
E. Wenkert et al., *Acc. Chem. Res.,* 7, 46-51, (1974).
C.S. Huber et al., *Can. J. Chem.,* 49, 3258-3271, (1971).
K. Likhitwitayawuid et al., *J. Nat. Prod.,* 56, 30-38, (1993).
H.H Lee et al., *Anti-cancer Drug Design,* 14, 487-497, (1999).
F. Hyafil et al., *Cancer Res.,* 534595-4602, (1993).
M.E. Wall et al., *J. Med. Chem.,* 37, 1465-1470, (1994).
F.J. Sharom et al., *Biochem. Pharmacol.,* 58, 571-586, (1999).
M.N. Prichard et al., *Antiviral Res.,* 14, 181-206, (1990).
Q. Mi et al., *Cancer Res., 61*, pp. 4030-4037, (2001).

* cited by examiner

TROPANE ALKALOID MULTIDRUG RESISTANCE INHIBITORS FROM ERYTHROXYLUM PERVILLEI AND USE OF THE SAME

CROSS REFERENCE TO RELATED APPLICATION

This application claims the benefit of U.S. provisional application Ser. No. 60/283,394, filed Apr. 12, 2001.

STATEMENT OF GOVERNMENTAL INTEREST

The subject matter of this application has been supported in part by research Grant No. CA52956 from the National Institutes for Health (NIH), Bethesda, Md.

FIELD OF THE INVENTION

The present invention relates to tropane alkaloid multidrug resistance inhibitors derived from *Erythroxylum pervillei,* and to methods of using the alkaloids in therapeutic treatments. More particularly, the present invention is directed to pervilleines A through F and pervilleine A N-oxide, and especially pervilleines A, B, and C, and their use in the treatment of diseases, such as a cancer.

BACKGROUND OF THE INVENTION

A serious problem associated with cancer chemotherapy is the development of multidrug-resistant (MDR) tumor cells during the course of treatment. An important mechanism of acquiring the MDR phenotype in mammalian cells is the enhanced expression of a membrane glycoprotein, termed Pgp (Reference 1). Pgp, having a molecular weight of 170 kDa, is coded by the MDR1 gene.

Pgp functions as an energy-dependent multidrug membrane transporter that rapidly extrudes a variety of hydrophobic antitumor drugs from target cancer cells, and thereby prevents the drugs from exerting cytotoxic effects. Initial physiological and pharmacological studies with multidrug-resistant mutant cell lines correlated resistance to reduced accumulation of drugs within the cell due to increased efflux or decreased influx (1). Because the efflux pump is an ATP-dependent transport system (2), agents that are good inhibitors of ATP-dependent drug transport should inhibit the efflux of hydrophobic drugs from resistant cells and increase intracellular accumulation. Accordingly, a variety of agents have been reported to overcome or at least partially circumvent MDR (3).

First-generation modulators originally were developed for other therapeutic indications (4). Included in this category are calcium channel blockers, such as verapamil (5), the immunosuppressive agent cyclosporin A (6), analogues of the anti-hypertensive reserpine and yohimbine (7), the neuroleptic agent, trifluroperazine (4), and antiestrogens, such as tamoxifen (1). Second-generation modulators were developed that lacked the pharmacological activities of the first-generation compounds and usually possessed higher affinity for Pgp. These agents include the R isomer of verapamil (8), a nonimmunosuppressive analogue of cyclosporin D, SDZ PSC-833 (6), and others such as MS-209 (9), S-9788 (10), GF120918 (11), and LY335979 (4).

While many of these pharmacological agents have been found to completely overcome drug resistance in in vitro models, the number of reports showing such phenomena in in vivo systems is more limited (12–15). The lack of in vivo activity of chemosensitizers results mainly from problems associated with maintaining active doses without causing serious side effects (16). Thus, clinical phase I and phase I/II studies often have been disappointing because of limited tolerance to prototype MDR inhibitors by themselves, which precluded attainment of potentially active levels in patients (11, 17).

For example, full reversion of MDR by verapamil requires a concentration of approximately 10 $\mu$M in most cell culture models, whereas plasma levels above 1 $\mu$M result in atrioventricular blocks (5, 18). Immunosuppressive effects and nephrotoxicity limit the clinical usefulness of cyclosporin A (6), and toxicities, such as cerebellar ataxia and hyperbilirubinemia, are caused by SDZ PSC-833 (19, 20). Also, cyclosporin A, verapamil, and SDZ PSC-833 have profound effects on the pharmacokinetics of doxorubicin, etoposide, and other oncolytic drugs (4).

As recently reported (21), the MDR modulator valspoday is being evaluated in phase III, randomized trials for the treatment of AML, multiple myeloma, and ovarian cancer. Also, Ontogen Corporation has announced completion of a phase I study conducted with the MDR-reversing agent OC 144-093 (22) and a second phase I study to examine oral administration is underway.

One part of a natural product drug discovery program involves monitoring the potential of plant extracts to reverse multiple drug resistance. Standard cell survival assays are used to determine the dose of plant extracts or compounds required to inhibit cell growth by 50% ($IC_{50}$) with drug-sensitive human epidermoid carcinoma parental KB-3 cells and Pgp-associated multidrug-resistant KB-V1 cells. To investigate the potential of plant extracts or compounds to reverse multidrug-resistance, KB-V1 cells are treated with different concentrations of plant extracts or compounds in the presence (1 $\mu$g/ml) or absence of vinblastine. This concentration of vinblastine is lethal to KB-3 cells, but does not affect the growth of KB-V1 cells. Therefore, KB-3 cells serve as a control to differentiate between nonspecific cytotoxicity and selective MDR antagonism.

The assay employs 96-well microtiter plate technology, and over 3,000 different plant extracts have been tested. Using the model for bioassay-guided isolation of active principles, four moderate inhibitors of MDR have been identified: coronaridine, conoduramine, voacamine, and (–)-roemerine (23, 24).

The present invention, therefore, is directed to additional multidrug resistance inhibitors that are isolated from *Erythroxylum pervillei* and overcome the problem associated with prior inhibitors.

SUMMARY OF THE INVENTION

The present invention is directed to tropane alkaloid multidrug resistance inhibitors, and their use in therapeutic applications. In particular, the present invention is directed to tropane alkaloid multidrug resistance inhibitors derived from *Erythroxylum pervillei,* and to the therapeutic use of such inhibitors. The present invention also is directed to inhibitors disclosed herein that are synthesized, as opposed to isolated from an *Erythroxylum pervillei* extract and purified.

Therefore, one aspect of the present invention is to provide multidrug resistance inhibitors derived from *Erythroxylum pervillei* and use of the inhibitors in a method of modulating the efflux capability of a P-glycoprotein (Pgp) in a cell or tissue by contacting the cell or tissue with an effective amount of the multidrug resistance inhibitor.

Another aspect of the present invention is to provide a method of potentiating the activity of a therapeutic drug in a cell or tissue by contacting the cell or tissue with a multidrug drug resistance inhibitor from *Erythroxylum pervillei* that modulates the efflux capability of a Pgp.

In particular, the efflux capability of the Pgp can be selectively inhibited to retain a therapeutic drug, like a chemotherapeutic drug or antibiotic drug, in the cell, while maintaining normal efflux capabilities with respect to other compounds.

Still another aspect of the present invention is to provide an improved composition for treating a disease or condition comprising:

(a) a therapeutic drug useful in the treatment of the disease or condition, and (b) a compound derived from *Erythroxylum pervillei* and capable of selectively inhibiting the efflux capability of a Pgp with respect to the therapeutic drug. For example, the disease or condition is a cancer or an infection, and the therapeutic drug is a chemotherapeutic drug or an antibiotic, respectively.

As used herein, an "infection" is defined as a bacterial, viral, parasitic, or other microbiological infection, and diseases and conditions resulting therefrom.

Another aspect of the present invention is to provide a pharmaceutical composition comprising (a) a compound selected from the group consisting of pervilleine A, pervilleine B, pervilleine C, pervilleine D, pervilleine E, pervilleine F, pervilleine A N-oxide, and mixtures thereof, and (b) a pharmaceutically acceptable carrier.

Another aspect of the present invention is to provide an article of manufacture comprising: (a) a packaged anticancer compound and (b) a package insert describing coordinated administration to a patient of said anticancer compound and a compound selected from the group consisting of pervilleine A, pervilleine B, pervilleine C, pervilleine D, pervilleine E, pervilleine F, and pervilleine A N-oxide. The above articles of manufacture optionally can include packaged pervilleine A, pervilleine B, pervilleine C, pervilleine D, pervilleine E, pervilleine F, or pervilleine A N-oxide.

These and other aspects of the present invention will become apparent from the following nonlimiting, detailed description of the preferred embodiments.

DETAILED DESCRIPTION OF THE PREFERRED EMBODIMENTS

Figure 1:
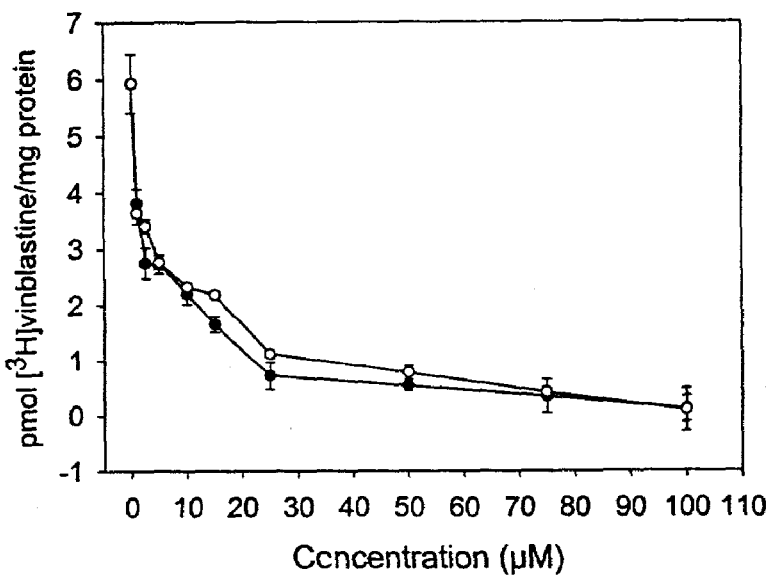
FIG. 1 contains a plot pmol [$^3$H]vinblastine/mg protein vs. concentration of verapamil and pervilleine A.

P-Glycoprotein-mediated drug efflux can yield a multidrug-resistance (MDR) phenotype that is associated with a poor response to cancer chemotherapy. In accordance with an important feature of the present invention, extremely potent novel tropane alkaloid aromatic esters that overcome MDR were obtained from a chloroform-soluble extract derived from the roots of *Erythroxylum pervillei* Baillon (Erythroxylaceae) (25). *Erythroxylum pervillei* Baill. (Erythroxylaceae) was collected in Madagascar. This plant is known locally as "Tsivano" and has several folkloric uses, including as a fish poison, and to treat abdominal pain and tumors.

Certain species from the plant genus *Erythroxylum* (family Erythroxylaceae) are used in traditional medicine to treat amenorrhea, hemorrhage, kidney disorders, influenza, sinusitis, upset stomach, and to combat fatigue, the feeling of hunger, and as stimulants (52–54). Extracts of some *Erythroxylum* species have shown biological activity, such as antiinflammatory, analgesic, and antimicrobial effects (54, 55). Tropane alkaloids are known to be present in *Erythroxylum*, and some are currently used in medicine (56–58). However, their activity as potential anticancer agents has not yet been investigated.

The compounds isolated from *Erythroxylum pervillei* have been termed pervilleines, and are tropane alkaloids obtained from a chloroform extract of *Erythroxylum pervillei* as the result of bioactivity-guided fractionation. Starting with crude plant material, pervilleine A was obtained in 0.042% w/w yield, and pervilleines B and C also were obtained in good yield (0.035% and 0.045% w/w, respectively).

The pervilleines were found to restore the vinblastine sensitivity of cultured multidrug-resistant KB-V1 and CEM/VLB$_{100}$ cells, with IC$_{50}$ values for pervilleine A, for example, of 0.36 and 0.02 $\mu$M, respectively. Similarly, the chemosensitivity of KB-8-5 cells to colchicine was restored with an IC$_{50}$ value for pervilleine A of 0.61 $\mu$M. Pervilleines B and C were found to restore the vinblastine sensitivity of cultured multidrug-resistant KB-VI cells, with IC$_{50}$ values of 0.17 $\mu$M for each compound.

The mechanism of this response was evaluated using a number of model systems. First, incubation of multidrug resistant KB-V1 and CEM/VLB$_{100}$ cells with up to 45 $\mu$M pervilleine A for 72 hours did not significantly affect either the transcription of MDR1, as revealed by reverse transcriptional-PCR-based analysis of MDR1 mRNA, or levels of Pgp, as shown by Western blots. ATP-dependent binding of [$^3$H]vinblastine observed with isolated multidrug-resistant KB-V1 cell membrane vesicles was inhibited by pervilleine A in a dose-dependent manner, and kinetic analysis indicted competitive inhibition with respect to vinblastine binding with a K$_i$ of 7.3 $\mu$M. Consistent with this effect, intracellular accumulation of [$^3$H]vinblastine was increased from 0.18 pmol [$^3$H]vinblastine/50×10$^4$ cells to approximately 5 pmol [$^3$H]vinblastine/50×10$^4$ cells in the presence of 40 $\mu$M pervilleine A.

As described herein, the mechanism by which pervilleine A, B, and C, or the other pervilleines, reverse the MDR phenotype has been partially characterized. However, cancer treatments that appear promising with in vitro models are often less effective against solid tumors. One method of providing a preliminary indicator of therapeutic efficacy has been described recently by Hollingshead et al. (26). The majority of the human tumor cell lines currently employed in cell culture can be grown inside hollow fibers (27) to form a heterogeneous solid tumor model. Therefore, semipermeable hollow fibers containing human tumor cells are implanted at the intraperitoneal or subcutaneous compartments of host mice, and the mice are treated with the test substances of interest. Through determination of the potential to inhibit cell growth versus potential to mediate a toxic response toward the host, a preliminary estimate of therapeutic efficacy is provided in a cost- and time-effective manner (28). This model was used for assessing MDR reversing agents in combination with conventional chemotherapeutic agents, and the results were obtained for pervilleine A, B, and C.

Therefore, to explore the potential relevance of the above responses, KB-V1 or KB-8-5 cells were placed in hollow fibers and implanted into NCr nu/nu mice. Cell growth was not significantly inhibited when vinblastine or pervilleine A, B, or C were administered as single agents, but when used in combination, inhibitions of up to 75% for pervilleine A, and up to 77.5% for pervilleines B and C, were observed. Equimolar doses of verapamil were less effective. These data indicate that pervilleine A, B, and C are effective inhibitors of P-glycoprotein.

In accordance with an important feature of the present invention, and a chloroform-soluble extract of the Madagascan plant, *Erythroxylum pervillei* Baill. (Erythroxylaceae), gave a pronounced selective inhibitory activity for a multidrug-resistant human cancer cell line (KB-V1) assessed in the presence of the antineoplastic drug, vinblastine (VLB). Chromatographic fractionation, using this cell line to monitor purification, led to the isolation and structural characterization of nine tropane aromatic ester alkaloids.

Seven of these compounds are new, and have been assigned the trival names "pervilleines A–F" and "pervilleine A N-oxide." The procedures used for the isolation and structural characterization of these seven new compounds are described hereafter. Also described is the single-crystal X-ray diffraction of one of the two known compounds obtained, tropane-3α,6β,7β-triol 3-phenylacetate. The structures of pervilleines A–F, pervilleine A N-oxide, and verapamil are shown below:

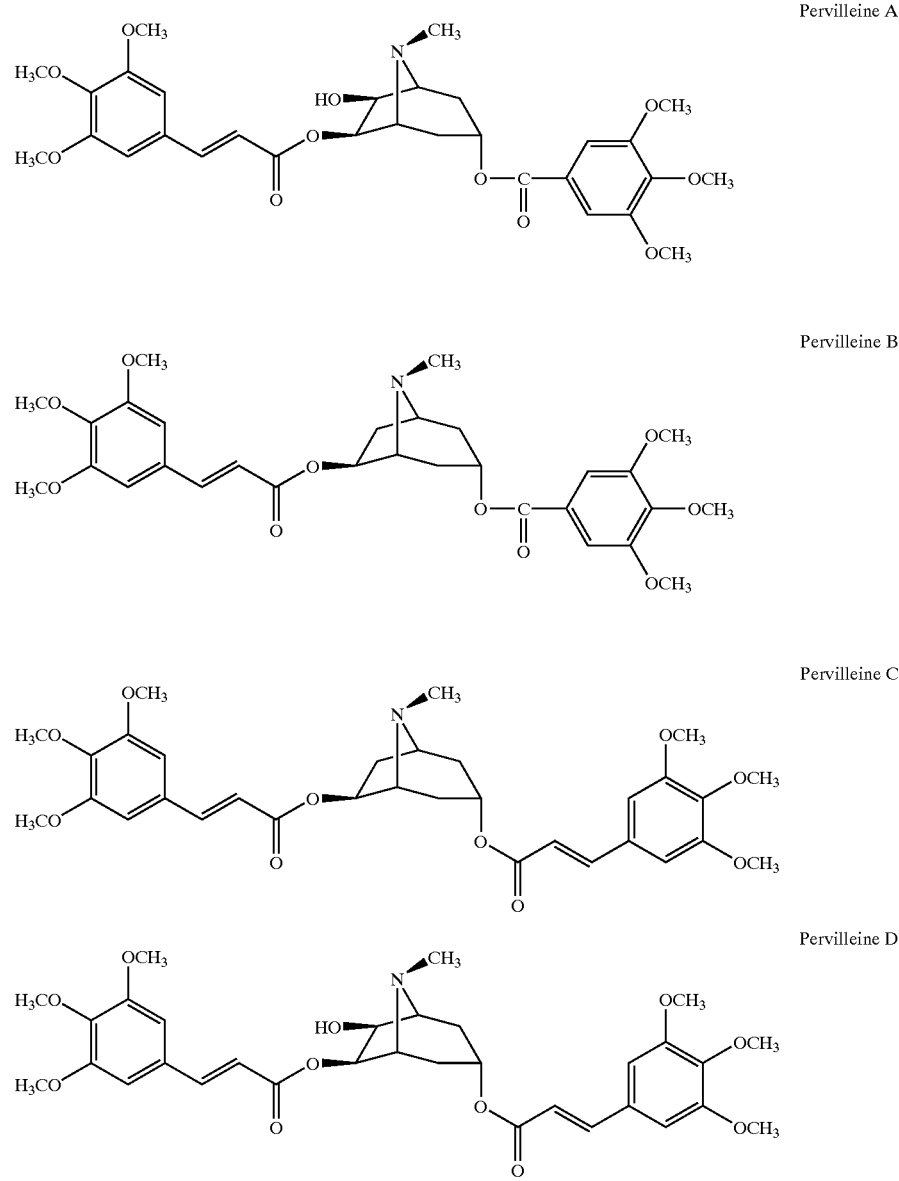

Pervilleine A

Pervilleine B

Pervilleine C

Pervilleine D

-continued

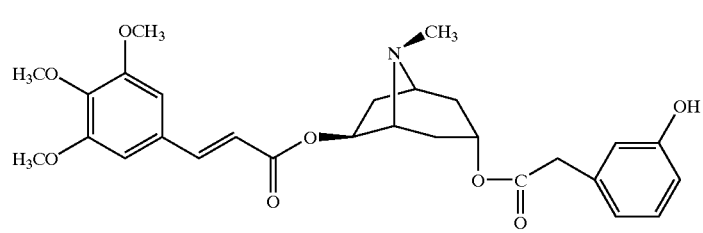

Pervilleine E

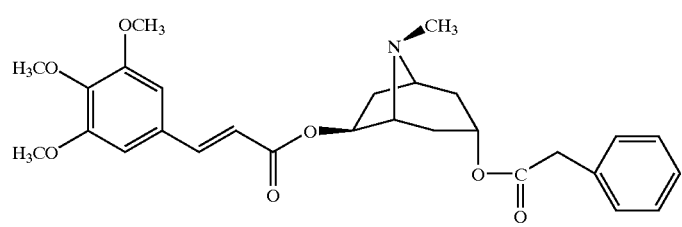

Pervilleine F

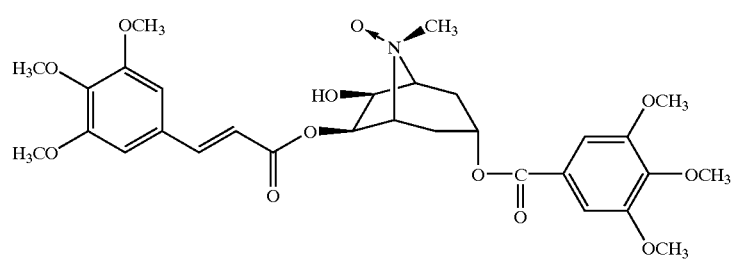

Pervilleine A N-oxide

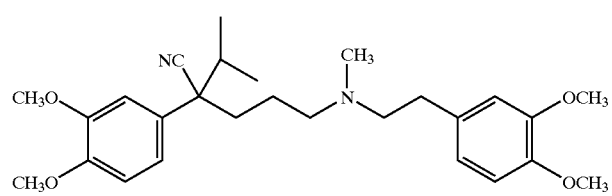

Verapamil

The pervilleines compared favorably as inhibitors of the multidrug resistance (MDR) phenotype with several standard MDR inhibitors, including verapamil, cyclosporin A, and GR120918 {N-{4-[2-(1,2,3,4-tetrahydro-6,7-dimethoxy-2-isoquinolinyl)-ethyl]-phenyl}-9,10-dihydro-5-methoxy-9-oxo-4-acridone carboxamide. Pervilleines A–C are particularly potent, and represent a new chemotype of MDR inhibitor. These new natural products exhibit advantages over other MDR inhibitors, such as improved efficacy, reduced toxicity, and/or a reduced incidence of undesired ancillary pharmacological effects.

The pervilleines were subjected to both preliminary and more focused biological testing. For example, Tables 3–5, respectively, summarize the following biological experiments: in vitro cytotoxicity of these compounds in a human tumor cell panel; multidrug resistance inhibition in an ovarian cancer cell line; and in vitro multidrug resistance modulation in some cell lines available at the National Cancer Institute. The conclusions from these experiments are: several of the pervilleines showed substantial selectivity for a multidrug-resistant cell line (KB, oral epidermoid) in the presence of vinblastine (Table 8); pervilleines B and C reversed drug resistance in a multidrug-resistant human ovarian adenocarcinoma (SKVLB) cell line with potency comparable to the acridone carboxamide multidrug resistance (MDR) modulator GR120918 (Table 4); pervilleines B–D and F exhibited comparable potency to verapamil and cyclosporin A in increasing the cytotoxicity of the standard substance (DINIB) (Table 5).

Additional biological evaluation on pervilleine A was performed, and the effects on the reversal of multidrug resistance of pervilleine A contrasted with those of verapamil in KB-V1 and KB-V-8 cells (Table 6) and CEM/VLB$_{100}$ cells (Table 7). In an in vivo study performed with the NCI hollow fiber model, KB-V1 and KB-8-5 cells were placed in hollow fibers and implanted into NCr nu/nu mice (Table 10 and FIG. 5). Cell growth was not significantly inhibited when vinblastine or pervilleine A were administered as single agents, but when used in combination, inhibition of up to 75% was observed. These data further confirm that pervilleine A is an effective inhibitor of P-glycoprotein. The biological activity of pervilleine A was extremely potent. This is the first time that the hollow fiber model has been used with a combination drug regimen to demonstrate reversal of the multidrug-resistance (MDR) phenotype. Similar positive results were obtained in the hollow fiber assay for pervilleines B and C.

In the present invention, a chloroform-soluble extract of E. pervillei was found to significantly inhibit the growth of a multidrug-resistant (MDR) KB-V1 cell line in the presence of vinblastine (VLB), while being much less cytotoxic for KB-V1 cells in the absence of VLB or normal KB cells. The nine tropane alkaloid aromatic esters (compounds 1–9) were isolated from the roots of *Erythroxylum pervillei* (Erythroxylaceae) by following potential to reverse multidrug-resistance with oral epidermoid carcinoma (KB-V1) cells. All isolates, including seven new structures (i.e., compounds 3–9), were evaluated against a panel of human cancer cell lines. Alkaloids 3 and 5–9 showed greatest activity with KB-V1 cells assessed in the presence of vinblastine, indicating that these compounds are potent modulators of P-glycoprotein. Confirmatory results were obtained with human ovarian adenocarcinoma (SKVLB) cells assessed in the presence of adriamycin, and synergistic studies performed with several cell lines from the NCI tumor panel. The structures of the compounds were determined using spectroscopic techniques. Single-crystal X-ray analysis was performed on the monoester, tropane-3α,6β,7β-triol 3-phenylacetate (compound 1).

In particular, activity-guided fractionation led to the isolation of nine tropane alkaloid aromatic esters (compounds 1–9), including seven new compounds, pervilleine A, pervilleine A N-oxide, and pervilleines B–F (compounds 3–9) (Chart 1). These compounds were isolated, identified, and structurally determined, and their cytotoxic activity and their action as modulators of multidrug resistance determined.

CHART 1

Tropane alkaloids isolated from *Erythroxylum pervillei*

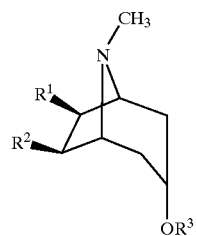

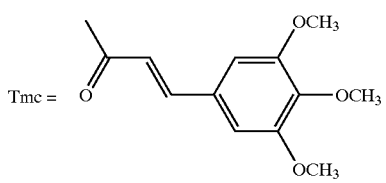

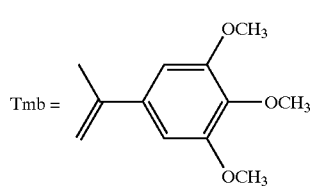

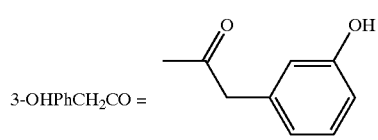

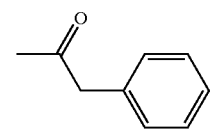

| | R¹ | R² | R³ | Other |
|---|---|---|---|---|
| 1 | OH | OH | PhCH₂CO | — |
| 2 | H | H | Tmb | — |

CHART 1-continued

Tropane alkaloids isolated from *Erythroxylum pervillei*

| | R¹ | R² | R³ | Other |
|---|---|---|---|---|
| 3 | OH | OTmc | Tmb | — |
| 4 | OH | OTmc | Tmb | N→O |
| 5 | H | OTmc | Tmb | — |
| 6 | H | OTmc | Tmc | — |
| 7 | OH | OTmc | Tmc | — |
| 8 | H | OTmc | 3-HOPhCH₂CO | — |
| 9 | H | OTmc | PhCH₂CO | — |

The air-dried powdered roots of *E. pervillei* were extracted with methanol, and, after removal of solvent, the residue was suspended in aqueous methanol (9:1) and washed with hexane. The aqueous methanol-soluble then was partitioned with chloroform. The chloroform-soluble extract showed significant inhibitory activity against a vinblastine-resistant KB (oral epidermoid carcinoma) cell line, KB-V1, assessed in the presence of VLB (KB-V1⁺, $ED_{50}$ 5.4 µg/mL). The residue then was subjected to a series of cytotoxicity-guided aluminum oxide column chromatographic purification steps, using this assay to monitor fractionation, to afford nine alkaloids (i.e., compounds 1–9).

Compounds 1 and 2 were identified as the known alkaloids, tropane-3α,6β,7β-triol 3-phenyl-acetate (59) and 1αH,5αH-tropan-3α-yl 3,4,5-trimethoxybenzoate (60), by comparison to published data. Compounds 3–9 are novel tropane alkaloids having different acyl substituents, and their structures were assigned by extensive use of $^1$H-, $^{13}$C-, one-dimensional selective INEPT, and 2D NMR spectroscopic techniques.

A single-crystal X-ray analysis was performed on compound 1, crystallized as white needles from methanol, in order to establish the stereochemistry of the N-methyl group. The final R factor was 6%, and the goodness of fit, 1.22. It was determined that the N-methyl group in this compound is axial.

Compound 3 has a molecular formula of $C_{30}H_{37}NO_{11}$, as determined from its high-resolution electronic impact mass spectrum (HREIMS). Its IR spectrum exhibited absorption bands at 3500 (OH), 1711 (ester), 1642 (α,β-unsaturated C=O), 1585 (aromatic C=C), 1220, and 1128 cm$^{-1}$ (C—O). The $^1$H-NMR spectrum of compound 3 revealed characteristic resonances for a tropane alkaloid skeleton trisubstituted at the C-3, C-6, and C-7 positions with signals at δ 5.37 (1H, br t, ca. J=4.5 Hz, H-3β), δ5.66 (1H, dd, J=6.9, 2.9 Hz, H-6α), and δ 4.77 (1H, d, J=6.9 Hz, H-7α) (Table 1), respectively (59). The downfield chemical shift and multiplicity for the H-3 signal indicated that C-3 bears an acyl moiety in a configuration (59–61). The above-mentioned coupling constants for the H-6α and H-7α chemical shifts accounted for the presence of exo substituents at the C-6 and C-7 positions, and the downfield shifts of H-6 and H-7 clearly indicated the substitution of an acyl moiety and a hydroxyl moiety at C-6 and C-7, respectively (61). A singlet at δ 2.62 (3H) was assigned to an N—CH$_3$ group, with H-1 and H-5 appearing as broad singlets at δ 3.27 (2H), and the H-2 and H-4 resonances observed at δ 2.37 (2H, m, H-2ax and H-4ax) and δ 1.74 (2H, br d, J=12.6 Hz, H-2eq and H-4eq) (Table 1). The $^{13}$C-NMR profile of the aliphatic carbons in compound 3 also was consistent with a C-3, C-6, C-7 trisubstituted tropane nucleus with signals at δ 67.5 (C-3), δ 77.7 (C-6), and δ 75.3 (C-7). The resonances at δ 26.4 and δ 26.3 were assigned to C-2 and C-4, respectively, while the C-1 and C-5 signals appeared, in turn, at 65.8 and 62.7 ppm, and finally, the N—CH$_3$ signal resonated at δ 34.6 (61, 62) (Table 2).

TABLE 1

$^1$H-NMR (δ, CDCl$_3$, J in parentheses) Data of Compounds 3–9[a]

| Proton | 3 | 4 | 5 | 6 | 7 | 8 | 9 |
|---|---|---|---|---|---|---|---|
| 1 | 3.22 br s | 4.32 br s | 3.41 br d (7.4) | 3.39 br d (7.2) | 3.18 br s | 3.27 br s | 3.26 br d (6.3) |
| 2ax | 2.37 m | 2.46–2.56 m | 2.33 br dd (11.4, 5.4) | 2.25 m | 2.31 m | 2.41 m | 2.00–2.23 m |
| 2eq | 1.74 br d (12.6) | 2.38 br d (16.9)[b] | 1.93 br d (11.7)[b] | 1.90 br d (15.3)[b] | 1.69 dd (15.3, 7.3) | 1.71 br d (15.2) | 1.78 br d (15.2)[b] |
| 3β | 5.37 br t (4.5) | 5.36 br t (4.5) | 5.34 br dd (5.4, 4.5) | 5.21 br t (5.0) | 5.24 br t (4.5) | 5.07 br t (5.2) | 5.05 br t (5.2) |
| 4ax | 2.37 m | 2.46–2.56 m | 2.33 dd | 2.25 m | 2.37 m | 2.37 m | 2.00–2.23 m |
| 4eq | 1.74 br d (12.6) | 2.31 br d (17.3)[b] | 1.72 br d (12.6)[b] | 1.69 br d (15.3)[b] | 1.69 dd (15.3, 7.3) | 1.45 br t (15.2) | 1.48 br d (15.2)[b] |
| 5 | 3.27 br s | 3.85 br s | 3.29 br s | 3.31 br s | 3.32 br s | 3.27 br s | 3.18 br s |
| 6α | 5.66 dd (6.9, 2.9) | 5.97 d (6.9) | 5.77 dd (7.5, 2.7) | 5.73 dd (7.6, 2.7) | 5.72 d (6.3) | 5.66 dd (7.5, 3.0) | 5.35 dd (7.5, 3.0) |
| 7α/αβ | 4.77 d (6.9) | 4.81 d (6.9) | 2.20–2.25 m | 2.22–2.26 m | 4.77 d (6.3) | 2.02 m | 2.00–2.23 m |
| NCH$_3$ | 2.62 s | 3.31 s | 2.61 s | 2.59 s | 2.60 s | 2.55 s | 2.50 s |
| Tmc | | | | R$^2$/R$^3$ | R$^2$/R$^3$ | | |
| α | 6.45 d (15.8) | 6.54 d (15.9) | 6.37 d (15.9) | 6.38/6.35 d (15.8) | 6.36/6.47 d (15.9) | 6.40 d (15.9) | 6.37 d (15.9) |
| β | 7.64 d (15.8) | 7.67 d (15.9) | 7.56 d (15.8) | 7.31/7.56 d (15.8) | 7.62/7.74 d (15.9) | 7.66 d (15.9) | 7.58 d (15.9) |
| ortho | 6.76 s | 6.77 s | 6.57 s | 6.74/6.88 s | 6.75/6.92 s | 6.77 s | 6.76 s |
| OCH$_3$ | 3.89–4.00 (3 s) | 3.88–3.97 (3 s) | 3.88–3.98 (3 s) | 3.88–3.94 (6 s) | 3.90–3.96 (6 s) | 3.89–3.90 (3 s) | 3.88–3.90 (3 s) |
| | Tmb | Tmb | Tmb | | | 3-HOPhCH$_2$CO | PhCH$_2$CO |
| CH$_2$ | | | | | | 3.56 s | 3.66 s |
| 2' | 7.35 s | 7.36 s | 7.38 s | | | 7.19 d (2.2) | 7.25–7.36 m |
| 3' | | | | | | | 7.25–7.36 m |
| 4', 6' | | | | | | 6.80–6.84 m | 7.25–7.36 m |
| 5' | 7.35 s | 7.36 s | | | | 7.22 t (7.8) | 7.25–7.36 m |
| OCH$_3$ | 3.89–4.00 (3 s) | 3.88–3.97 (3 s) | 3.88–3.98 (3 s) | | | | |

[a]Spectra recorded on a Varian XL300 instrument in CDCl$_3$ using TMS as internal standard. Values are given in ppm.
[b]Assignments bearing the same superscript may be exchanged in each column.

TABLE 2

$^{13}$C-NMR Data of Compounds 3–9 (Taken in CDCl$_3$ at 90 MHz using TMS as internal standard)[a]

| carbon | 3 | 4 | 5 | 6 | 7 | 8 | 9 |
|---|---|---|---|---|---|---|---|
| 1 | 65.8 | 76.9 | 64.8[c] | 64.9[b] | 65.8 | 64.3[b] | 65.0 |
| 2 | 26.4[b] | 32.4 | 31.1[b] | 31.0[c] | 26.3[b] | 30.9[b] | 30.9[b] |

TABLE 2-continued $^{13}$C-NMR Data of Compounds 3–9 (Taken in CDCl$_3$ at 90 MHz using TMS as internal standard)$^a$

| carbon | 3 | 4 | 5 | 6 | 7 | 8 | 9 |
|---|---|---|---|---|---|---|---|
| 3 | 67.5 | 62.3 | 67.6 | 67.1 | 66.8 | 67.4 | 67.3 |
| 4 | 26.3$^b$ | 33.5 | 32.5$^b$ | 32.5$^c$ | 26.2$^b$ | 32.0$^b$ | 32.4 |
| 5 | 62.7 | 78.4 | 59.1$^c$ | 59.0$^b$ | 62.7 | 58.9 | 58.9 |
| 6 | 77.7 | 74.9 | 78.9 | 79.3 | 77.8 | 79.9 | 78.9 |
| 7 | 75.3 | 74.7 | 37.3 | 37.2 | 75.1 | 37.2 | 35.8 |
| NCH$_3$ | 34.6 | 49.2 | 38.6 | 38.4 | 34.5 | 38.1 | 38.4 |
| Tmc | | | | R$^2$/R$^3$ | R$^2$/R$^3$ | | |
| C=O | 166.5 | 165.9 | 166.4 | 165.9/166.8 | 166.7/165.7 | 168.2 | 166.5 |
| α | 116.7 | 116.7 | 117.5 | 117.6/117.4 | 117.1/116.9 | 116.8 | 117.5 |
| β | 145.4 | 145.4 | 144.6 | 145.2/144.6 | 145.5/145.3 | 146.1 | 144.6 |
| 1' | 129.7 | 129.8 | 129.8 | 129.8/129.8 | 129.7/129.7 | 129.5 | 129.8 |
| 2', 6' | 105.2 | 105.1 | 105.1 | 105.4/105.1 | 105.5/105.2 | 105.4 | 105.2 |
| 3', 4', 5' | 153.4 | 153.4 | 153.3 | 153.4/153.4 | 153.4/153.4 | 153.4 | 153.4 |
| m-MeO | 56.2 | 56.1–56.4 | 56.1 | 56.2$^d$/56.1$^d$ | 56.2/56.2 | 56.2 | 56.1 |
| p-MeO | 61.0 | 62.3 | 61.0 | 61.0/60.9 | 60.9/61.0 | 61.0 | 61.0 |
| | Tmb | Tmb | Tmb | | | 3-HOPhCH$_2$CO | PhCH$_2$CO |
| C=O | 164.8 | 165.0 | 165.3 | | | 170.1 | 170.4 |
| CH$_2$ | | | | | | 42.7 | 42.2 |
| 1' | 125 | 123.7 | 125.3 | | | 134.7 | 133.8 |
| 2' | 106.5 | 106.6 | 106.5 | | | 116.8 | 128.7 |
| 3' | 153.4 | 153.3 | 153.8 | | | 156.9 | 129.3 |
| 4' | 153.1 | 153.2 | 153.5 | | | 114.9 | 127.1 |
| 5' | 153.4 | 153.3 | 153.8 | | | 130.0 | 129.3 |
| 6' | 106.5 | 106.6 | 106.5 | | | 121.0 | 128.7 |
| m-MeO | 56.3$^b$ | 60.9 | 56.1 | | | | |
| p-MeO | 60.9 | 56.1 | 60.9 | | | | |

$^a$Values are given in ppm. Data are based on APT, selective INEPT and 1D-HETCOR experiments.
$^{b-d}$Assignments bearing the same superscript may be exchanged in each column.

The acyl moieties of compound 3 were identified as 3,4,5-trimethoxycinnamoyl (Tmc) and 3,4,5-trimethoxybenzoyl (Tmb) units, with two signals at δ 6.45 (1H, d, J=15.8 Hz) and 7.64 (1H, d, J=15.8 Hz) assignable to the trans olefinic protons of the cinnamoyl residue, and two singlets at δ 6.76 (2H) and 7.35 (2H) attributed to the ortho aromatic protons of the cinnamoyl and benzoyl moieties, respectively (61). Signals for 18H (6x-OCH$_3$, δ 3.89–4.00) confirmed the presence of three methoxyl substituents symmetrically distributed in each unit (61, 63). Further support for the identities of these substituents was obtained from the EIMS fragments at m/z 375 (M$^+$–TmbA, 6%) and m/z 349 (M$^+$–TmcA 10%) (53, 61, 63). The NMR data (Tables 1 and 2) for the Tmc and Tmb units were in agreement with those published in the literature (61, 63, 64). The positions of attachment of the Tmc and Tmb moieties to the nucleus were determined by several selective INEPT NMR experiments (65). Thus, irradiation of H-6 (δ 5.66; $^3J_{CH}$=6 Hz) enhanced the carbonyl carbon signal at 166.5 ppm, which was similarly enhanced by selective irradiation of the vinylic protons at δ 7.64/6.45 (H-β/α), indicating that the Tmc residue is attached to C-6. In the same way, the Tmb moiety was placed at C-3 by irradiation of H-3 (δ 5.37) and the Tmb aromatic protons (δ 7.35) with the corresponding enhancement of the carbonyl carbon signal at δ 164.8. The N-methyl group was assigned as axial, by analogy with compound 1. Thus, compound 3 was determined as the new tropane alkaloid 3α-(3,4,5-trimethoxybenzoyloxy)-6β-(3,4,5-trimethoxycinnamoyloxy)-7β-hydroxy tropane, and has been accorded the trivial name, pervilleine A.

The NMR spectral data of compound 4 resembled those of pervilleine A (compound 3), with proton signals for H-3β at δ 5.36 (1H, br t, J=4.5 Hz), H-6α at δ 5.97 (1H, d, J=6.9 Hz), H-7α at δ 4.81 (1H, d, J=6.9 Hz) and their corresponding carbons at δ 62.3 (C-3), 74.9 (C-6), and 74.7 (C-7) (Tables 1 and 2), suggesting the presence of hydroxyl and diacyl substituents in the tropane nucleus. The acyl moieties were identified as Tmc and Tmb (Tables 1 and 2) and were placed at C-3 and C-6, respectively, by a sequence of selective INEPT experiments carried out as described for compound 3. A prominent ion at m/z 588 (56%) in the CIMS (positive mode) corresponding to the pseudo-empirical formula of C$_{30}$H$_{37}$NO$_{11}$ was observed for compound 4, the same molecular formula determined for compound 3. If compound 4 were an isomer of pervilleine A (compound 3), this would not satisfactorily explain the strong deshielding observed for H-1 (1H, br s, δ 4.32), H-2eq (1H, br d, δ 2.38), H-4eq (1H, br d, δ 2.31), and H-5 (1H, br s, δ 3.85), and the downfield shift for the N—CH$_3$ signal (δ 3.31 s). This effect also was observed for the corresponding carbons in the $^{13}$C-NMR spectra, which were assigned by APT, 1D- and 2D-HETCOR experiments (Table 2). The presence of a protonated molecular ion at m/z 604 ([M+1]$^+$, 7%) in the FABMS (positive mode) showed a 16 amu difference from the molecular weight of compound 3, and the decomposition of the product when subjected to EIMS, suggested that compound 4 could be an N-oxide of pervilleine A. Wenkert and coworkers (66) have compared the $^{13}$C-NMR data of scopolamine N-oxide and scopolamine free base, and observed significant changes on the chemical shifts of the neighboring carbons, leading to differences [Δδ$_C$ (scopolamine N-oxide scopolamine)] of +11.4 (C-1, C-5), −4.7 (C-3), −2.5 (C-6, C-7) and +9.0 (N—CH$_3$). The changes in the analogous chemical shifts observed for compound 4 and pervilleine A (compound 3) were Δδ$_C$+11.1 (C-1), +15.7 (C-5), −5.2 (C-3), −2.8 (C-6), −0.6 (C-7) and +14.6 (N—CH$_3$), which were clearly indicative of N-oxide substitution in alkaloid compound 4. While most of the Δδ$_C$ values matched literature values (66), the small observed differences can be explained based on the unsymmetrical substitution of the tropane nuclei in compound 3 and compound 4. Moreover, analysis of the $^1$H NMR spectrum of compound 4 showed the N—CH³ signal at δ 3.31. Huber and coworkers (67) demonstrated by applying X-ray crystallographic and NMR studies a clear correlation of the configuration and the ¹H-NMR chemical shift of the N-methyl group in scopolamine N-oxide. The axial methyl was found to resonate at δ 3.39, while the stereoisomeric equatorial methyl occurred at δ 3.60. Based on these observations, the N-methyl group in compound 4 corresponds to an axial configuration, consistent with the X-ray crystallographic study performed on compound 1. Thus, compound 4 was identified as 3α-(3,4,5-trimethoxybenzoyloxy)-6β-(3,4,5-trimethoxycinnamoyloxy)-7β-hydroxytropane N-oxide (pervilleine A N-oxide).

Compound 5 also showed similar spectroscopic data to those of pervilleine A (compound 3). The molecular formula was $C_{30}H_{37}NO_{10}$ as obtained by HREIMS, 16 amu lower than that of compound 3, suggesting the lack of a hydroxyl group in the molecule of compound 5. The ¹H-NMR spectrum exhibited characteristic signals for a disubstituted tropane nucleus at the C-3 and C-6 positions with signals appearing for H-3β at δ 5.34 (1H, br dd, J=5.4, 4.5 Hz), H-6α at δ 5.77 (1H, dd, J=7.5, 2.7 Hz) and $CH_2$-7 at δ 2.20–2.25 (2H, m) (Table 9). The acyl moieties were deduced as Tmc and Tmb, and the positions of their attachment were determined as for compound 3. Accordingly, compound 5 was identified as 3α-(3,4,5-trimethoxybenzoyloxy)-6β-(3,4,5-tri-methoxycinnamoyl-oxy)-tropane, and was given the trivial name pervilleine B.

Compound 6 was assigned a molecular formula of $C_{32}H_{39}NO_{10}$, as determined by HREIMS, and showed the same pattern of substitution as that of compound 5 with resonances for H-3β at δ 5.21 (1H, br t, J=5.0 Hz), H-6α at δ 5.73 (1H, dd, J=7.6, 2.7 Hz), and $CH_2$-7 at δ 2.22–2.26 (2H, m). However, signals for a Tmb moiety were not evident in the ¹H- and ¹³C-NMR spectra of compound 6, and the signals for the Tmc moiety were duplicated (Tables 1 and 2). Hence, the structure of compound 6 (pervilleine C) was elucidated as 3α,6β-di-(3,4,5-trimethoxycinnamoyloxy)tropane.

Compound 7 was assigned a molecular formula of $C_{32}H_{39}NO_{11}$ (HREIMS), and showed similar signals for the tropane nucleus in the ¹H-NMR spectrum to compound 3, with signals seen for H-3β (δ 5.24; 1H, br t, J=4.5 Hz), H-6α (δ 5.72; 1H, d, J=6.3 Hz), and H-7α (δ 4.77; 1H, d, J=6.3 Hz) The portion of the ¹H-NMR spectrum depicting the acyl groups of compound 7 was closely comparable to equivalent data for compound 6, with resonances observed at δ 7.74/7.62 (1H each, d, J=15.9 Hz, Hb), 6.47/6.36 (1H each, d, J=15.9 Hz, Hα), and 6.92/6.75 (2H each, s, H-2', H-6'). The ¹³C-NMR spectrum also supported the presence of two Tmc moieties in compound 7 (Table 2). On basis of the above evidence, the structure of compound 7 was therefore characterized as 3α,6β-di-(3,4,5-trimethoxycinnamoyloxy)-7β-hydroxytropane (pervilleine D).

The NMR spectral data for compounds 8 and 9, when compared with the spectra for the above-mentioned analogues, exhibited values consistent with the presence of one Tmc substituent and one other acyl substituent in each compound. The tropane nucleus showed NMR resonances in agreement with those of compound 5, suggesting disubstitution at the C-3 and C-6 positions. The coupling constants for H-3 (brt, J=5.2 Hz) and H-6 (dd, J=7.5, 3.0 Hz) indicated a β and α configuration, respectively, for these protons in 8 and 9 (Table 1). Compound 8, with a molecular formula of $C_{28}H_{33}NO_8$, as determined by HREIMS, showed in the ¹H-NMR spectrum resonances at δ 3.56 (2H, s), 7.19 (1H, d J=2.2 Hz), 6.80–6.84 (2H, m), and 7.22 (1H, d J=7.8 Hz) and carbon signals at δ 170.1, 42.7, 134.7, 116.8, 156.9, 114.9, 130.0, and 121.0, indicating the presence of a 3-hydroxyphenylacetyl moiety (59). Selective INEPT experiments were used to confirm the substitution patterns of the Tmb unit at C-6 and the 3-hydroxyphenylacetyl group at C-3. The molecular formula of compound 9 was determined by HREIMS as $C_{28}H_{33}NO_7$, 16 amu lower than that of compound 8, suggesting there is no hydroxyl group present in compound 9. Analysis of the NMR data showed that the second acyl group was a phenylacetyl unit (59). Selective INEPT experiments led to the placement of the Tmb unit at C-6 and the phenylacetyl group at C-3 for this alkaloid. Based on the evidence presented above, the structures of compounds 8 and 9 were elucidated as 3α-(3-hydroxyphenylacetoxy)-6β-(3,4,5-trimethoxycinnamoyloxy)tropane (pervilleine E) and 3α-phenylacetoxy-6β-(3,4,5-trimethoxycinnamoyloxy)tropane (pervilleine F), respectively.

The stereochemistry at the different asymmetric carbons for pervilleines A–F (compounds 3, 5–9) and pervilleine A N-oxide (compound 4) was determined on the basis of NMR coupling constant observations, and confirmed using molecular modeling experiments (PCMODEL Version 4.0). In this regard, different stereoisomer combinations were minimized using the MMX force field, wherein predicted coupling constants were compared with the experimental J values actually obtained finding the best matching with the stereoisomers presented herein. All structures are numbered clockwise starting from the bridgehead methine and representing arbitrarily one of the two possible enantiomers. The N-methyl group is presented in its axial configuration for pervilleines A–F (compounds 3, 5–9) according to the structure established for compound 1 by means of X-ray crystallographic analysis.

Alkaloids 1–9 initially were tested against a panel of human cancer cell lines according to established protocols (68). Pervillines A and F (compounds 3 and 9) showed both strong activity and selectivity for the multidrug-resistant KB-Vl cell line in the presence of vinblastine ($ED_{50}$, 0.3 and 0.2 µg/mL, respectively), while pervilleine E (compound 8) exhibited selectivity, but potency was reduced by approximately one order of magnitude ($ED_{50}$, 1.9 µg/mL). Pervilleines B–D (compounds 5–7) displayed high potency with KB-Vl cells assessed in the presence of VLB, but were less selective. Pervilleine A N-oxide (compound 4), as well as the known compounds 1 and 2 were shown to be inactive ($ED_{50} \geq 20$ µg/mL) for all cell lines, including KB-V1 in the presence of VLB (Table 3).

Several observations concerning structural requirements for activity within this compound group may be made from the cytotoxicity panel data of alkaloids 1–9 shown in Table 3. When compounds 1–3 and 5–9 are considered specifically, a C-6 Tmc ester substituent appeared essential for the elicitation of significant activity against KB-V1 cells in the presence of VL. The absence of a hydroxyl group at C-7, as in pervilleines B (compound 5) and C (compound 6), led to approximately the same cytotoxic potency shown by pervilleines A (compound 3) and D (compound 7) for KB-V1 cells in the presence of VLB, but reduced selectivity when the other cell lines in the panel are considered. Pervilleine E (compound 8), esterified at C-3 with a 3-hydroxyphenylacetyl moiety, exhibited less potency and less selectivity than pervilleine D (compound 7) with a Tmc ester at C-3. When the C-3 Tmc ester at C-3 (pervilleine C) was altered to a phenylacetyl group (pervilleine F), less potency but greater selectivity resulted. Pervilleine A N-oxide (compound 4) was not significantly active for any cell lines represented in the tumor panel. However, it is known that some N-oxides are bioreductive drugs (69, 70), compound 4 could serve as a prodrug and be metabolized to release the active pervelline A (compound 3).

In Table 4, the cytotoxic activities of pervilleines A–C (compounds 3, 5, 6) and pervilleine A N-oxide are compared with the acridonecarboxamide derivative GF120918 (20), an MDR inhibitor, in ovarian adenocarcinoma (SKOV3) and multidrug-resistant ovarian adenocarcinoma (SKVLB) cell lines, performed as previously described (72). When 1 $\mu$M adriamycin was added to the latter cell line, pervilleines B and C (IC$_{50}$ 0.12 and 0.08 $\mu$M, respectively) mediated potent responses that were comparable to GR120918 (IC$_{50}$ 0.02 $\mu$M). Because the data in Tables 3 and 4 indicate that the tropane alkaloid esters evaluated were less toxic for KB-V1 and SKVLB cells than their normal counterparts in the absence of any additional drug, the compounds may be substrates for the MDR transporter, and may exhibit a competitive mechanism for MDR inhibition.

Alkaloids 5–7 and 9 were further evaluated for their efficacy as potential modulators of P-glycoprotein. This assay assessed the ability of these test compounds to increase the cytotoxicity of an agent of the MDR phenotype {4,9-dihydro-3-iso-butyl-2-methyl-1-(p-nitrophenacyl)-4,9-dioxo-1H-naphth[2-3-d]imidazolium bromide (DINIB)}, compared with an agent not of the MDR phenotype (5-flurouracil), used as a negative control (73, 74). Evaluation of the data for the alkaloids tested indicated that pervilleines B and C are excellent modulators of MDR. Their synergy values at a 95% confidence level showed effects comparable in potency with two standard MDR inhibitors, verapamil, and cyclosporin A (Table 5). The dose ranges selected for the pervilleines evaluated were appropriate to produce full dose-response curves (except for 7 which induced limited toxicity at 50 ng/mL). Maximum escalation of DINIB toxicity was measured at nontoxic concentrations of the pervilleines at least four- to ten-fold below the concentration required to produce 50% growth inhibition in the cells.

TABLE 3

In Vitro Cytotoxicity of Alkaloids 1–9 in a Human Tumor Panel[a]

| Compound | ED$_{50}$ ($\mu$g/mL) | | | | | | | |
|---|---|---|---|---|---|---|---|---|
| | BC1 | Lu1 | Col2 | KB | KB-V1$^+$ | KB-V1$^-$ | LNCaP | SW626 |
| 1 | >20 | >20 | >20 | >20 | >20 | >20 | >20 | >20 |
| 2 | >20 | >20 | >20 | >20 | >20 | >20 | >20 | >20 |
| 3 | >20 | >20 | >20 | >20 | 0.3 | >20 | >20 | >20 |
| 4 | >20 | >20 | >20 | >20 | >20 | >20 | >20 | >20 |
| 5 | 9.4 | 3.1 | 1.3 | >20 | 0.1 | 8.8 | 1.0 | 3.2 |
| 6 | 2.8 | 2.3 | 4.1 | 2.2 | 0.1 | 9.0 | >20 | 1.4 |
| 7 | 15.0 | 15.1 | 4.9 | 11.0 | 0.2 | 9.0 | 14.1 | 6.5 |
| 8 | >20 | >20 | 13.4 | 14.7 | 1.9 | >20 | >20 | 8.4 |
| 9 | >20 | >20 | 4.9 | >20 | 0.2 | >20 | >20 | >20 |

[a]Key to human cancer cell lines used:
BC1, breast cancer;
Lu1, lung cancer;
Col2, colon cancer;
KB, oral epidermoid carcinoma;
KB-V1$^+$, drug resistant KB assessed in presence of vinblastine (1 $\mu$g/mL);
KB-V1$^-$, drug-resistant KB assessed in the absence of vinblastine;
LNCaP, hormone-dependent prostate cancer;
SW626, human ovarian adenocarcinoma.

TABLE 4

Multidrug Resistance Inhibition by Tropane Alkaloids 3–6.
IC$_{50}$ ($\mu$M)

| Compound | SKOV3 (pGp − ve)[a] | BSKVLB (pGp + ve)[b] | SKVLB (pGp + ve)[c] |
|---|---|---|---|
| adriamycin | 0.008 | 2.2 | — |
| GB120918[d] | 8.1 | 14 | 0.02 |
| pervilleine A (3) | >10 | >10 | 0.65 |
| pervilleine A N-oxide (4) | >10 | >10 | >10 |
| pervilleine B (5) | 3.8 | >10 | 0.12 |
| pervilleine C (6) | 2.8 | >10 | 0.08 |

[a]SKOV3 (ovarian adenocarcinoma; provided by Dr. V. Lin, Ontario Cancer Institute).
[b]SKVLB (ovarian adenocarcinoma, multidrug resistance; provided by Dr. V. Lin, Ontario Cancer Institute).
[c]Addition of 1 $\mu$m adriamycin.
[d]N-{4-[2-(1,2,3,4-tetrahydro-6,7-dimethoxy-2-isoquinolinyl)-ethyl]-phenyl}-9,10-dihydro-5-methoxy-9-oxo-4-acridine carboxamide.

TABLE 5

In vitro Multidrug Resistance Modulation of Alkaloids 5–7 and 9

| Compound | Concentration used ($\mu$g/mL)[a] | Cell line[b] | | | |
|---|---|---|---|---|---|
| | | HCT-15 | UO-31 | CAKI-1 | LOX IMVI |
| verapamil | 12.5 | 696.8 | 432.1 | 369.8 | 185.1 |
| cyclosporin A | 6.3 | 719.1 | 642.1 | 273.3 | 72.9 |
| pervilleine B (5) | 12.5 | 607.6 | 248.7 | 268.1 | 33.3 |
| pervilleine C (6) | 3.1 | 946.7 | 444.0 | 332.3 | 32.6 |
| pervilleine D (7) | 50.0 | 758.3 | 562.7 | 387.9 | 13.2 |
| pervilleine F (9) | 25.0 | 714.7 | 364.4 | 342.1 | 59.2 |

[a]Concentration required to produce less than 20–30% growth inhibition.
[b]Key to human cancer cell lines:
HCT-15, colon;

TABLE 5-continued

In vitro Multidrug Resistance Modulation of Alkaloids 5–7 and 9

| Compound | Concentration used (µg/mL)[a] | Cell line[b] | | | |
|---|---|---|---|---|---|
| | | HCT-15 | UO-31 | CAKI-1 | LOX IMVI |

UO-31, renal;
CAKI-1, renal;
LOX IMVI, melanoma.
The ability of potential modulators to increase the cytotoxicity of 4,9-dihydro-3-isobutyl-2-methyl-1-(p-nitrophenyl)-4,9-dioxo-1H-naphth[2,3-d]imidazolium bromide (DINIB; $1 \times 10^{-4}$ M) was evaluated, and results represent synergy values at a 95% confidence level.
Values <25 are insignificant,
25–50 are minor but significant,
50–100 indicate moderate synergy, and
>100 indicate strong synergy and are probably important in vivo (73, 74).

In summary, nine aromatic tropane alkaloid esters have been isolated from the roots of *Erythroxylum pervillei* (Erythroxylaceae). Seven of these alkaloids are new compounds, namely, pervilleine A, pervilleine A N-oxide, and pervilleines B–F. All of these new tropane derivatives were found to contain a trans-3,4,5-trimethoxycinnamoyloxy unit at the C-6 position, with the C-3 hydroxyl group being differentially esterified and the C-6 sometimes being hydroxylated among alkaloids 3–9. The known compounds tropane-3α,6β,7β-triol 3-phenyl-acetate (compound 1) and 1αH,5αH-tropan-3α-yl 3,4,5-trimethoxybenzoate (compound 2) also were obtained, with the configuration of the N-methyl group of compound 1 established as axial by X-ray crystallographic analysis.

Several of these compounds showed substantial selectivity for a MDR-resistant human oral epidermoid (KB) cell line in the presence of vinblastine, with pervilleines A, B, C, D, and F all showing a similar cytotoxic potency against this cell line. In a MDR-resistant human ovarian adenocarcinoma (SKVLB) cell line in the presence of adriamycin, pervilleines B and C reversed drug resistance with potency comparable to the acridone carboxamide MDR modulator GR120918 (70). In a further in vitro biological test protocol, compounds 5–7 and 6 were found to exhibit comparable potency to verapamil and cyclosporin at increasing the cytotoxicity of DINIB (73, 74). The mode of action facilitated by these tropane alkaloids has been partially characterized, and synergistic activity has been demonstrated in the in vivo hollow fiber model using KB-V1 and KB-8-5 cells (75).

Experimental Section

Abbreviations: AML, acute myeloid leukemia; BSA, bovine serum albumin; cDNA, complementary deoxyribonucleic acid; DEPC, diethylpyrocarbonate; DMEM, Dulbecco's Modified Eagle Medium; MeOH, methanol; $NH_4OH$, ammonium hydroxide; $CHCl_3$, chloroform; $Et_2NH$, diethylamine; DMSO, dimethyl sulfoxide; EDTA, ethylenediaminetetraacetic acid; dNTP, deoxynucleotide triphosphate; $IC_{50}$, 50% inhibitory concentration; MDR, multidrug-resistance; MTD, maximum tolerated dose; MTT, 3-(4,5-dimethylthiazol-2yl)-2,5-diphenyltetrazolium bromide; PA, pervilleine A [3α-(3,4,5-trimethoxybenzoyloxy)-6β-(3,4,5-trimethoxycinnamoyloxy)-7β-hydroxytropane]; PB, pervilleine B [3α-(3,4-5-trimethoxybenzoyloxy)-6β-(E)-(3,4,5-trimethoxycinnamoyloxy)tropane]; PC, pervilleine C [3α,6β-di(E)-(3,4,5-trimethoxycinnamoyloxy)tropane]; PBS, phosphate-buffered saline; Pgp, P-glycoprotein; PVP, polyvinylpyrrolidone; SDS, sodium dodecyl sulfate; VP, verapamil.

General procedures. Melting points were determined on a Fisher-Johns melting point apparatus and are uncorrected. Optical rotations were measured on a Perkin-Elmer 241 polarimeter. UV spectra were recorded with Nicolet MX-1 spectrophotometer, and IR spectra were taken on a Beckman DU-7 instrument. NMR spectra were obtained in $CDCl_3$ with TMS as an internal standard. $^1$H-NMR and $^{13}$C-NMR spectra, selective INEPT, HETCOR and NOE experiments were recorded on either a Nicolet NMC-360 or a Varian XL-300 instrument. The EIMS, HREIMS, and HRFABMS data were obtained on a Finnigan MAT-112S mass spectrometer. Open column chromatography was carried out over silica gel G (70–230 mesh; E. Merck, Darmstadt, Germany), or aluminum oxide (alumina, neutral, Brockman Activity I, 60–325 mesh; Fisher Chemicals, Pittsburgh, Pa.), using gradient mixtures of $CHC_{13}$-acetone-28% $NH_4OH$ or hexane-acetone-28% $NH_4OH$ as solvents, respectively. TLC plates (silica gel 60 $F_{254}$ glass plates, 0.25 mm layer thickness; E. Merck) were visualized under UV light, using Dragendorff's spray reagent.

Plant material. The roots of *E. pervillei* were collected in a southern semiarid region of Madagascar in October 1992. A voucher specimen (A00362) is deposited in the John G. Searle Herbarium, Field Museum of Natural History, Chicago, Ill.

Extraction and isolation. The air-dried powdered roots of *E. pervillei* (12 kg) were extracted with MeOH two times to afford a residue (129 g) which was then suspended in MeOH—$H_2O$ (9:1, 800 mL), and washed with hexane (3×500 mL). The aqueous layer was concentrated under a vacuum and then partitioned between 5% MeOH (600 mL) and $CHCl_3$ (3×400 mL). The $CHCl_3$-soluble extract (28 g) showed significant activity against a vinblastine-resistant KB cell line (KB-V1 assessed in the presence of 1 µg/mL vinblastine; KB-V1$^+$, $ED_{50}$ 5.4 µg/mL), while the aqueous layer was inactive against this cell line. The active extract (28 g) was absorbed on silica gel and purified by silica gel column chromatography using gradient mixtures of $CHCl_3$-acetone-28% $NH_4OH$ (20:10:0.1→5:20:1) as solvent systems to yield five major alkaloid-containing fraction mixtures (fractions 1–5). Fraction 1 (0.8 g) was purified by passage on a neutral aluminum oxide ($Al_2O_3$) column eluted with hexane-acetone-MeOH-$Et_2NH$ (9:1:0.1:0.1) to afford 5 (420 mg) and 9 (450 mg). Fractions 2 and 3 were combined (4.5 g) and subjected to $Al_2O_3$ column chromatography using hexane-acetone-MeOH-$Et_2NH$ gradient mixtures (6:1:0.1:0.1→3:1:0.1:0.1) to afford compounds 1 (4 mg), 2 (450 mg), 6 (520 mg), and 8 (480 mg). Fraction 4 (1.9 g) was subjected to passage over an $Al_2O_3$ column using hexane-acetone-MeOH-$Et_2NH$ (3:1:0.1:0.1) as eluent to afford compounds 3 (500 mg), 7 (510 mg), and additional quantities of 1 (42 mg). Fraction 5 (62 mg) was worked up by preparative TLC using acetone-$H_2O$-28% $NH_4OH$ (4:0.75:2 drops) mixture as solvent system to afford compound 4 (14 mg, $R_f$ 0.47).

Tropane-3α,6β,7β-triol 3-phenylacetate (compound 1). White crystals (MeOH); mp 120–122° C.; $^1$H, $^{13}$C NMR, and EIMS data, consistent with literature values (59).

1αH,5αH-Tropan-3α-yl 3,4,5-trimethoxy-benzoate (compound 2). White amorphous solid; mp 238–240° C.; $^1$H NMR and EIMS data, consistent with literature values (60).

Pervilleine A [3α-(3,4,5-trimethoxybenzoyloxy)-6β-(3,4, 5-trimethoxycinnamoyloxy)-7β-hydroxytropane] (compound 3). White amorphous solid, softened at 46–48° C.;

[α]$_D$ −0.6° (c 0.18, CHCl$_3$); UV λ$_{max}$ (MeOH) 302.5 nm (log ε 4.39); IR ν$_{max}$ (film) 3500, 2944, 1711, 1642, 1585, 1505, 1472, 1416, 1345, 1265, 1220, 1128, 1057, 1004 cm$^{-1}$; $^1$H-NMR and $^{13}$C-NMR data, see Tables 1 and 2; EIMS m/z 587 (4) [M$^+$], 375 (6) [M$^+$−TmbA], 349 (10) [M$^+$−TmcA], 273 (19), 231 (29), 137 (100) [M$^+$−TmcA−TmbA]; HREIMS m/z found 587.2360. calcd for C$_{30}$H$_{37}$NO$_{11}$, 587.2367.

Pervilleine A N-oxide [3α-(3,4,5-trimethoxybenzoyloxy)-6β-(3,4,5-trimethoxycinnamoyloxy)-7β-hydroxytropane N-oxide] (compound 4). White amorphous solid, softened at 114° C., mp 118°–121° C.; [α]$_D$ +1.46°) (c 0.28, CHCl$_3$); UV λ$_{max}$ (MeOH) 303.0 nm (log ε 4.24); IR ν$_{max}$ 2944, 1717, 1688, 1588, 1500, 1468, 1420, 1338, 1278, 1220, 1130, 1004, 759 cm$^{-1}$; 1H-NMR and $^{13}$C-NMR data, see Tables 1 and 2; CIMS m/z 604 (6) [M+H$^+$], 588 (56) [M+H$^+$−O], 281 (43) [M+H$^+$−C(6)HTmc−C(7)HOH], 239 (32) [TmcA+H$^+$], 213 (100) [TmbA+H$^+$]; HRFABMS m/z found 604.2407 (M$^+$+1). calcd for C$_{30}$H$_{37}$NO$_{12}$+H, 604.2394.

Pervilleine B [3α-(3,4,5-trimethoxybenzoyloxy)-6β-(3,4,5-trimethoxy cinnamoyloxy)tropane] (compound 5). White amorphous solid, mp 40–42° C.; [α]$_D$ −22.5° (c 0.25, CHCl$_3$); UV λ$_{max}$ (MeOH) 302.5 nm (log ε 4.31); IR ν$_{max}$ 2944, 1711, 1641, 1585, 1505, 1472, 1416, 1345, 1220, 1127, 1004 cm$^{-1}$; $^1$H-NMR and $^{13}$C-NMR data, see Tables 1 and 2; EIMS m/z 571 (50) [M$^+$], 360 (100) [M$^+$−TmbA], 307 (3) [M$^+$−C(6)HTmc−C(7)H$_2$], 238 (18) [TmcA$^+$], 221 (41) [TmcO$^+$], 212 (22) [TmbA$^+$]; HREIMS m/z found 571.2421. calcd for C$_{30}$H$_{37}$NO$_{10}$, 571.2417.

Pervilleine C [3α,6β-di-(3,4,5-trimethoxycinnamoyloxy) tropane] (compound 6). White amorphous solid, mp 53–57° C.; [α]$_D$ +29.0° (c 0.10, CHCl$_3$); UV λ$_{max}$ (MeOH) 305.0 nm (log ε 4.51); IR ν$_{max}$ 2944, 1711, 1641, 1585, 1504, 1472, 1454, 1345, 1270, 1167, 1127, 915, 745 cm$^{-1}$; $^1$H-NMR and $^{13}$C-NMR data, see Tables 1 and 2; EIMS m/z 597 (3) [M$^+$], 360 (100) [M$^+$−TmbA], 333 (4) [M$^+$−C(6)HTmc−C(7)H$_2$], 238 (18) [TmcA$^+$], 221 (41) [TmcO$^+$], 212 (22) [TmbA$^+$]; HREIMS m/z found 597.2552. calcd for C$_{32}$H$_{39}$NO$_{10}$, 597.2574.

Pervilleine D [3α,6β-di-(3,4,5-trimethoxycinnamoyloxy)-7β-hydroxytropane] (compound 7). White amorphous solid, mp 59–61° C.; [α]$_D$ +9.0° (c 0.10, CHCl$_3$); UV λ$_{max}$ (MeOH) 305.0 nm (log ε 4.50); IR ν$_{max}$ 2944, 1710, 1641, 1585, 1504, 915, 745 cm$^{-1}$; $^1$H-NMR and $^{13}$C-NMR data, see Tables 1 and 2; EIMS m/z 613 (6) [M$^+$], 375 (16) [M$^+$−TmcA], 333 (2) [M$^+$−C(6)HTmc−C(7)HOH], 238 (29) [TmcA$^+$], 221 (52) [TmcO$^+$], 190 (6), 154 (14), 137 (100) [M$^+$−2TmcA]; HREIMS m/z found 613.2526. calcd for C$_{32}$H$_{39}$NO$_{11}$, 613.2523.

Pervilleine E [3α-(3-hydroxyphenylacetoxy)-6β-(3,4,5-trimethoxycinnamoyloxy)-tropane] (compound 8). White amorphous solid, mp 53–57° C.; [α]$_D$ +29.0° (c 0.10, CHCl$_3$); UV λ$_{max}$ (MeOH) 305.0 nm (log ε 4.51); IR ν$_{max}$ 2944, 1711, 1641, 1585, 1504, 1472, 1454, 1345, 1270, 1167, 1127, 915, 745 cm$^{-1}$; $^1$H-NMR and $^{13}$C-NMR data, see Tables 1 and 2; EIMS m/z 511 (77) [M$^+$], 360 (100) [M$^+$-3-OHPhCH$_2$CO$_2$], 238 (17) [M$^+$−TmcO], 247 (39) [M$^+$−C(6)HTmc−C(7)H$_2$], 238 (17) [TmcA$^+$], 221 (39) [TmcO$^+$], 138 (45), 122 (63) [M$^+$−TmcA-3-OHPhCH$_2$CO$_2$]; HREIMS m/z found 511.2210. calcd for C$_{28}$H$_{33}$NO$_8$, 511.2206.

Pervilleine F [3α-phenylacetoxy-6β-(3,4,5-trimethoxycinnamoyloxy)-tropane] (compound 9). White amorphous solid, mp 59–61° C.; [α]$_D$ +9.0° (c 0.10, CHCl$_3$); UV λ$_{max}$ (MeOH) 305.0 nm (log ε 4.50); IR ν$_{max}$ 2944, 1710, 1641, 1585, 1504, 915, 745 cm$^{-1}$; $^1$H-NMR and $^{13}$C-NMR data, see Tables 1 and 2; EIMS m/z 495 (73) [M$^+$], 360 (100) [M$^+$—PhCH$_2$CO$_2$], 238 (29) [TmcA$^+$], 231 (49) [M$^+$−C(6)HTmcC(7)H$_2$], 221 (65) [TmcO$^+$], 136 (8) [PhCH$_2$CO$_2$H$^+$], 122 (70) [M$^+$−TmcA—PhCH$_2$CO$_2$]; HREIMS m/z found 495.2260. calcd for C$_{28}$H$_{33}$NO$_7$, 495.2257.

X-ray crystallographic analysis of tropane-3α,6β,7β-triol 3-phenylacetate (compound 1). Crystal data: C$_{16}$H$_{21}$NO$_4$, Mr=291.34, monoclinic, space group P2$_1$, a=6.5574(13), b=26.577(5), c=8.448(2) Å, β=102.08(3)°, V=1439.7(5) Å$^3$ (by least squares refinement on diffractometer angles for 12 automatically centered reflections), λ=1.54178 Å, Z=4, D$_c$=1.344 Mg/m$^{-3}$, F(000)=624, μ(Cu—Kα)=0.789 mm$^{-1}$. Crystal dimensions: 0.5×0.2×0.2 mm. Data Collection and Processing. Three-dimensional, room temperature (293° K) X-ray data were collected on a Rigaku AFC6S diffractometer with monochromatized Cu—Kα X-radiation, using the 2Θ/ω mode with scan range (ω) 3.33–57.47° plus Kα separation and a variable scan speed (4.88–14.65 min$^{-1}$). A total of 2158 reflections were measured (3<2Θ<115°, min. hkl 0 0 −9, max. hkl 7 29 9); 1968 independent reflections were obtained [R(σ)0.0240, Friedel opposites merged]. No absorption correction was applied. One control reflection monitored every 99 reflections showed no appreciable decay during 13.6 h of exposure of the crystal to X-rays. Structure Analysis and Refinement. Direct methods resulted in the location of all of the nonhydrogen atoms. Full-matrix least-squares refinement with anisotropic thermal parameters was used for all nonhydrogen atoms. Hydrogen atoms were refined in riding mode. Refinement converged at R=0.0631, R$_w$=0.1643. Maximum and mean shift/errors in the final cycle of refinement were 0.0415 and 0.0376, respectively. The final electron-density difference synthesis showed no peaks >0.194 or <−0.198 eÅ$^3$. All computations were carried out using SHELXTL for IRIS VB5,03 system of programs (76, 77).

Bioassay Evaluation Procedures

Cytotoxicity assay. Compounds 1–9 were evaluated for cytotoxic activity against a panel of human cancer cell lines, including KB-V1 in the presence and absence of VLB, according to an established protocol (68). Similar procedures were used with the ovarian cancer cell lines listed in Table 4 (72).

In vitro multidrug resistance assay. Compounds 5–7 and 9, were evaluated for efficacy as potential modulators of P-glycoprotein according to established protocols (73, 74).

Chemicals and Cell Cultures. [$^3$H]Vinblastine (4.8 Ci/mmol) was purchased from Moravek Biochemicals (Brea, Calif.). All other chemicals were purchased from Sigma Chemical Co. Cell culture media and supplements were obtained from Life Technologies, Inc. (Grand Island, N.Y.). Human oral epidermoid carcinoma KB-3 was purchased from the American Type Culture Collection (ATCC, Rockville, Md.), and KB-V1 and KB-8-5 cells were supplied by Dr. I. B. Roninson (Department of Molecular Genetics, University of Illinois at Chicago, Chicago, Ill.). KB-3 cells were maintained in DMEM medium supplemented with 10% heat-inactivated calf serum and PSF (100 units/ml penicillin G, 100 μg/ml streptomycin sulfate, 250 ng/ml amphotericin B). KB-V1 cells were grown in the same medium, which was further supplemented with vinblastine (1 μg/ml). Similarly, KB-8-5 cells were cultured in the same medium supplemented with colchicine (10 ng/ml). Human leukemic lymphoblasts CEM cells and their multidrug-resistant counterpart CEM/VLB$_{100}$ cells were cultured as described previously (29). Polyvinylidene fluoride (PVDF)

hollow fibers (500,000 Da molecular weight cut-off, 1.0 mm ID) were purchased from Spectrum Medical Industries (Luguan Hills, Calif.).

Cytotoxic potential. The cytotoxic potential of test substances with KB-3, KB-V1 and KB-8-5 cells was determined as described previously (24). Briefly, various concentrations of test compounds (dissolved in 10 µl of 10% DMSO) were transferred to 96-well plates, and 190 µl aliquots of cell suspensions ($5 \times 10^4$ cells/ml) were added to each well. The plates then were incubated for 72 hours at 37° C. (100% humidity with a 5% $CO_2$ atmosphere in air), and 100 µl of cold 20% aqueous trichloroacetic acid were added to the growth medium in each well to fix the cells. The cultures were incubated at 4° C. for 30 minutes, washed, air-dried, stained with sulforhodamine B solution, and washed with 1% acetic acid. Finally, 200 µl of 10 mM Tris base were added to each well and the optical densities were determined at 515 nm utilizing an ELISA plate reader. In each case, a zero-day control was performed by adding an equivalent number of cells to several wells and incubating at 37° C. for 30 minutes, and processing as described above. Optical density values obtained with the zero-day control were subtracted, and cell survival, relative to control (solvent-treated) cultures, was calculated. The cytotoxic potential of the compounds with CEM and CEM/$VLB_{100}$ cells was determined as described by Beck et al. (30). Cells were grown in 24-well plates at a density of $5-6 \times 10^5$ cells/ml. At 48 hours, the cell number was determined using a Coulter Counter, with a channelizer to distinguish cells from debris. The $IC_{50}$ was defined as the concentration of drug required to inhibit the 48 hr growth of treated cells by 50% compared with untreated controls.

[$^3$H]Vinblastine accumulation with KB-V1 vesicles. Cell membrane vesicles were prepared from KB-V1 cells following literature procedures (31, 32) with some modifications. Medium was removed from KB-V1 cells in log growth phase (about 80% confluence) and the cells were rinsed with ice-cold PBS followed by ice-cold PBS containing 2 mM EDTA. Aprotinin (1 mg/ml) was then added, and, after a 10 minutes incubation at room temperature, the cells were harvested by gentle aspiration with a serological pipette and collected by centrifugation (100×g for 5 minutes). The cells were suspended in 0.25 M sucrose buffer (0.01 M Tris-HCl, pH 7.5, containing 0.25 M sucrose, 0.2 mM $CaCl_2$, 1 mM EDTA) and homogenized with a Polytron at 2,500 rpm for 30 seconds. Following this procedure, <5% of the cells remained intact. The homogenate then was diluted with four volumes of 0.025 M sucrose solution (0.01 M Tris-HCl, pH 7.5, containing 0.025 M sucrose) and centrifuged (1,000×g for 10 minutes). The supernatant was layered onto a 35% sucrose cushion (35% w/v sucrose, 1 mM EDTA, 0.01 M Tris-HCl, pH 7.5) and centrifuged at 16,000×g for 30 minutes. The interface (about 5 ml) was collected and diluted with four volumes of 0.25 M sucrose, 0.01 M Tris-HCl, pH 7.5, and centrifuged at 100,000×g for 1 hour. The resulting vesicle pellet was suspended in PBS containing 1 mM phenylmethylsulfonyl fluoride, using a 25-gauge needle, and stored at −80° C. Protein content was determined using a bicinchoninic acid protein assay kit with BSA as a standard (33).

Vinblastine accumulation with membrane vesicles assays were performed in 96-well plates as described previously (23, 24). Plasma membrane vesicles (40 µg protein) were incubated in 0.01 M Tris-HCl buffer, pH 7.5, containing 0.125 M sucrose, 5 mM $MgCl_2$, 0.5 mM ATP, and 0.16 µM [$^3$H]vinblastine (4.8 Ci/mmol). Various concentrations of test samples, dissolved in 5 µl of DMSO, were then added (final volume, 100 µl), and incubations were conducted at ambient temperature for 20 minutes. For kinetic studies, various concentrations of [$^3$H]vinblastine were used. Reactions were terminated by aspirating the contents of each well onto a glass filter filter (printed type A filtermats, Wallac) using a 96-well harvester (Harvester 96, Tomtec). Radioactivity was determined by liquid scintillation counting (1450 Microbeta, Wallac). Nonspecific binding was determined by performing similar incubations with reaction mixtures containing a 1,000-fold excess of unlabeled vinblastine. Nonspecific binding was subtracted from all total-binding data to yield specific binding.

[$^3$H]Vinblastine accumulation with intact cells. Measurement of the accumulation of [$^3$H]vinblastine in cell monolayers was performed by the method of Fojo et al. (34) with some modifications. Studies were performed with 24-well plates. In preparing the cell monolayers, 2 ml of a cell suspension containing $2.5 \times 10^5$ cells per ml of incubation medium (DMEM with 10% calf serum) were added to each well. Control wells contained 2 ml of assay medium. Following the addition of [$^3$H]vinblastine (16 nM, 4.8 Ci/mmol) and various concentrations of test samples (dissolved in 10 µl of DMSO), the plates were incubated at 37° C. in a 5% $CO_2$ incubator for 1 hour. Monolayers were washed three times with cold PBS, dried by inversion, and the cells were treated with trypsin. Cell suspensions were then transferred to vials containing 3 ml of scintillation solution (CytoScint™, ICN), mixed vigorously, and counted. The quantity of [$^3$H]vinblastine associated with incubations containing cells was corrected by subtracting the counts associated with incubations not containing cells.

RT-PCR analysis of MDR1 mRNA expression. Culture flasks (60×15 mm) containing $100 \times 10^4$ KB-3, KB-V1, CEM or CEM/$VLB_{100}$ cells were treated with various concentrations of pervilleine A (0–34 µM) or verapamil (0–44 µM) for 72 hours at 37° C. in a 5% $CO_2$ incubator. Total RNA was isolated from cultured KB-3, KB-V1, CEM and CEM/$VLB_{100}$ cells with TRIzol reagent (Life Technologies, Inc.) (33), and quantified by UV absorbance. The reverse transcription of RNA was performed by using the SUPERScript™ Preamplification System (Life Technologies, Inc.) in a final volume of 21 µl containing 5×First Strain Synthesis Buffer, 2.5 mM $MgCl_2$, 0.5 mM each dNTP, 10 µM DTT, 2 units of RNAse inhibitor, 200 units of Super-Scrip II reverse transcriptase, 0.5 µg oligo $(dT)_{12-18}$, 2 µg of total RNA (3 µg for CEM and CEM/$VLB_{100}$ cells), and DEPC-treated water. After incubation at 42° C. for 50 minutes, the room temperature reaction was terminated by heating to 70° C. for 15 minutes. To the newly synthesized cDNA (2 µl), a PCR mixture containing 1.4 mM $MgCl_2$ (1.2 mM for CEM and CEM/$VLB_{100}$ cells), 2.5 units of Taq polymerase, 0.2 µmol (0.6 µmol for CEM and CEM/$VLB_{100}$ cells) of primers based on the MDR1 gene (35) and custom synthesized by Ana-Gen Technology, Inc. (Palo Alto, Calif.) (5'-ATAT-CAGCAGCCCACATCAT-3';    5'-GAAGCACTGGGAT-GTCCGGT-3') (35). As an internal control, 0.125 µmol (0.1 µmol for CEM and CEM/$VLB_{100}$ cells) of primers for GAPDH    (5'-CGGGAAGCTTGTGATCAATGG-3'; 5'-GGCAGTGATGGCATGGACTG-3') (36) were added (final volume to 50 µl). The PCR was heated to 94° C. for 3 minutes, and immediately cycled 23 times (35 times for CEM and CEM/$VLB_{100}$ cells) through a 1-minute denaturing step at 94° C., a 1-minute annealing step at 58° C., and a 1-minute elongation step at 72° C., with a Perkin-Elmer 2400 thermocycler. After the final cycle, a 7-minute elongation step at 72° C. was performed. Aliquots of PCR products were electrophoresed on 2% agarose gels (Bio-Rad), and PCR fragments were visualized with ethidium bromide staining.

Western blot analysis of MDR1 expression. To investigate MDR1 gene expression, western blots were performed with KB-3, KB-V1, CEM and CEM/VLB$_{100}$ cells treated with pervilleine A (0–45 µM) or verapamil (0–44 µM) for 72 hours at 37° C. in a 5% $CO_2$ incubator. Cells (7.5×10$^5$ cells as starting cell amount) were harvested using SDS lysis buffer [20 mM Tris-HCl (pH 6.8) containing 0.4% SDS (w/v), 5% glycerol (v/v), 0.006% bromophenol blue, 2% β-mer-captoethanol], and lysates were boiled for 10 minutes and stored at −20° C. Aliquots of lysates were used for protein determinations (bicinchoninic acid protein assay kit with BSA as standard), and equivalent amounts of protein were electrophoresed by SDS-PAGE with precast 7.5% Tris-glycine acrylamide gels (Novex, San Diego, Calif.). Following transfer to polyvinylidene difluoride membranes, nonspecific binding sites were blocked with 5% nonfat dry milk. Blotting was performed with rabbit polyclonal antibody mdr (Ab-1) (Oncogene Research Products, Inc.) and analyzed by streptavidin horseradish peroxidase-conjugated secondary antibody (Amersham Life Science) and visualized using a ECL western blotting detection system (Amersham Life Science).

In vivo hollow fiber test. In vivo hollow fiber test was performed using a literature procedure with some modifications (28). Confluent monolayers of KB-3, KB-V1 or KB-8-5 cells were harvested, collected by centrifugation and resuspended in conditioned medium at a concentration of 7.5×10$^5$ cells/ml. Fibers filled with cells were incubated in 6-well plates overnight at 37° C. in a 5% $CO_2$ atmosphere. Female athymic NCr nu/nu mice at 5–6 weeks of age were obtained from Frederick Cancer Research Facility. Each mouse hosted up to 6 fibers, which were cultured in two physiological compartments. For intraperitoneal implants, a small incision was made through the skin and musculature of the dorsal abdominal wall, the fiber samples were inserted into the peritoneal cavity in a craniocaudal direction and the incision was closed with skin staples. For subcutaneous implants, a small skin incision was made at the nape of the neck to allow insertion of an 11-gauge tumor implant trocar. The trocar, containing the hollow fiber samples, was inserted caudally through the subcutaneous tissues and fibers were deposited during withdrawal of the trocar. The incision was closed with a skin staple.

In preliminary studies, cell growth was assessed with fibers containing various cell densities. As a result, a cell density of 7.5×10$^5$ cells/ml was found to be suitable for drug studies for KB-3, KB-V1, and KB-8-5 cells. For treatment protocols, vinblastine and verapamil were dissolved in PBS; pervilleines A, B, and C were coprecipitated with PVP (37) to increase solubility, and then dissolved in PBS. Mice were randomized into 6 groups (3 mice per group): PBS vehicle control group; vinblastine treatment group; verapamil treatment group; pervilleine A, B, or C treatment group; verapamil plus vinblastine group; and pervilleine A, B, or C plus vinblastine group. Test compounds were administrated once daily by intraperitoneal injection from day 3–6 after implantation. Body weights were measure daily.

On day 7, mice were sacrificed and fibers were retrieved. The fibers were placed into 6-well plates, with each well containing 2 ml of fresh, prewarmed culture medium and allowed to equilibrate for 30 minutes at 37° C. To define the viable cell mass contained within the intact hollow fibers, a MTT dye conversion assay was used. Briefly, 1 ml of pre-warmed culture medium containing 1 mg MTT/ml was added to each dish. After incubating at 37° C. for 4 hours, the culture medium was aspirated and the samples were washed twice with normal saline containing 2.5% protamine sulfate solution by overnight incubation at 4° C. To assess the optical density of the samples, the fibers were transferred to 24-well plates, cut in half and allowed to dry overnight. The formazan was extracted from each sample with DMSO (250 µl/well) for 4 hours at room temperature on a rotation platform. Aliquots (150 µl) of extracted MTT formazan were transferred to individual wells of 96-well plates and assessed for optical density at a wavelength of 540 nm. The effect of the treatment regimen was determined by the net growth percentage of the cells relative to change in body weight.

Results

Growth inhibitory potential. An in vitro cell survival assay was employed as an initial method for monitoring the potential of test compounds to reverse multidrug-resistance. As summarized in Table 6, neither pervilleine A nor verapamil demonstrated appreciable growth inhibitory potential with KB-3 cells in culture. This cell line is highly susceptible to vinblastine ($IC_{50}$=0.04 µM) and colchicine ($IC_{50}$=0.05 µM). In the absence of vinblastine, neither test substrate inhibited the growth of KB-V1 cells ($IC_{50}$ values>34 or 44 µM for pervilleine A or verapamil, respectively). However, when vinblastine was added to the media in the presence of pervilleine A or verapamil, chemosensitivity was restored ($IC_{50}$=0.36 or 0.79 µM, respectively). For pervilleine A, these data yielded $IC_{50}$ ratios of 66.6 and >95 for KB-3/KB-V1 (+vinblastine) and KB-V1 (−vinblastine)/KB-V1 (+vinblastine), respectively, which compare favorably with the corresponding values obtained with verapamil (47 and >55, respectively), and indicated a lack of nonspecific cytotoxicity. For KB-8-5 cells (Table 6), even though pervilleine A showed greater growth inhibitory activity ($IC_{50}$=14 µM) than verapamil ($IC_{50}$>44 µM) in the absence of colchicine, the $IC_{50}$ ratios of KB-3/KB-8-5 (+colchicine) and KB-8-5 (colchicine)/KB-8-5 (+colchicine) were still favorable (40.3 and 23.3, respectively, for pervilleine A, and 13.1 and >15.4, respectively, for verapamil).

TABLE 6

Reversal of MDR in KB-V1 and KB-8-5 cells by pervilleine A and verapamil

| Cell Line | Pervilleine A | Verapamil |
| --- | --- | --- |
| KB-3 | 24[a] | 37[a] |
| KB-V1 (−)[b] | >34[a] | >44[a] |
| KB-V1 (+)[b] | 0.36[a] | 0.79[a] |
| KB-8-5 (−)[c] | 14[a] | >44[a] |
| KB-8-5 (+)[c] | 0.61[a] | 2.9[a] |
| KB-3/[KB-V1 (+)][b] | 66.6[d] | 47[d] |
| [KB-V1 (−)]/KB-V1 (+)][b] | >95[d] | >55[d] |
| KB-3/[KB-8-5 (+)][c] | 40.3[d] | 13.1[d] |
| [KB-8-5 (−)]/[KB-8-5 (+)][c] | 23.3[d] | >15.4[d] |

[a]Results are expressed as $IC_{50}$ values (concentration required to inhibit cell growth by 50%) in µM. Data are the means of the two independent experiments, with each concentration tested in triplicate.
[b]Incubations were performed in the presence (1 µg/ml) (+) or absence (−) of vinblastine.
[c]Incubations were performed in the presence (10 ng/ml) (+) or absence (−) of colchicine.
[d]Ratios of $IC_{50}$ values.

A related group of studies conducted with drug-resistant CEM/VLB$_{100}$ cells is summarized in Table 7. In the absence of vinblastine or daunorubicin, neither pervilleine A nor verapamil inhibited the growth of CEM/VLB$_{100}$ cells (IC$_{50}$>15 μM). In the presence of pervilleine A, the IC$_{50}$ values of vinblastine and daunorubicin were reduced to 0.02 and 0.065 μM, respectively, and the corresponding values in the presence of verapamil were 0.025 and 0.5 μM, respectively. These effects were specific, based on the high IC$_{50}$ ratios of Modulator/(Modulator+Vinblastine) and Vinblastine/(Modulator+Vinblastine), and the corresponding ratios obtained with daunorubicin (Table 7).

TABLE 7

MDR reversal ability in drug-resistant human leukemia CEM/VLB$_{100}$ cells.

| Experimental Conditions | Modulator | |
|---|---|---|
| | pervilleine A | verapamil |
| Modulator only | >15[a] | >15[a] |
| (Modulator + Vinblastine)[b] | 0.02[a] | 0.025[a] |
| Vinblastine/(Modulator + Vinblastine) | 250[c] | 200[c] |
| Modulator/(Modulator + Vinblastine) | >750[c] | >600[c] |
| (Modulator + Daunorubicin)[d] | 0.065[a] | 0.5[a] |
| Daunorubicin/(Modulator + Daunorubicin) | 15[c] | 2[c] |
| Modulator/(Modulator + Daunorubicin) | >231[c] | >30[c] |

[a]Results are expressed as IC$_{50}$ values (concentration required to inhibit cell growth by 50%) in μM. Data are the means of the two independent experiments, with each concentration being tested in duplicate.
[b]Pervilleine A concentration = 5 μM; verapamil concentration = 10 μM; vinblastine concentration, varied from 1 nM–10 μM. In the absence of modulator, the IC$_{50}$ value of vinblastine was 5 μM.
[c]Ratios of IC$_{50}$ values.
[d]Pervilleine A concentration = 5 μM; verapamil concentration = 10 μM; daunorubicin concentration, varied from 10 nM–100 μM. In the absence of modulator, the IC$_{50}$ value of daunorubicin was 1 μM.

As summarized in Table 8, neither pervilleine B nor verapamil demonstrated appreciable growth inhibitory potential with KB-3 cells in culture (>35 μM and 37 μM, respectively), but pervilleine C showed nonspecific toxicity (IC$_{50}$=3.7 μM). Compared with pervilleine A. (IC$_{50}$=24 μM), pervilleine B is less cytotoxic, but pervilleine C is more toxic with KB-3 cells. In the absence of vinblastine, neither test substrate significantly inhibited the growth of KV-V1 cells (IC$_{50}$ values 15, 15, or 44 μM for pervilleine B, pervilleine C, or verapamil, respectively). However, when vinblastine was added to the media in the presence of pervilleine B, pervilleine C, or verapamil, chemo-sensitivity was restored (IC$_{50}$=0.17, 0.17, or 0.79 μM, respectively). Even though pervilleine B or C showed greater growth inhibitory activity (IC$_{50}$=15 μM) than verapamil (IC$_{50}$=44 μM) in the absence of vinblastine, the IC$_{50}$ ratios of KB-V1 (–vinblastine)/KB-V1 (+vinblastine) were still favorable (88 for pervilleine B or C, and 56 for verapamil), indicating a relative lack of nonspecific cytotoxicity. With an IC$_{50}$ value >34 μM in the absence of vinblastine, 0.36 μM in the presence of vinblastine, and an IC$_{50}$ ratio of KB-V1 (–vinblastine)/–KB-V1 (+vinblastine) >95, pervilleine A appears somewhat superior to pervilleines B and C, but the effectiveness for all three compounds is of the same order of magnitude.

TABLE 8

Relationship of MDR-reversing activity and physicochemical properties of the modulators evaluated

| Compound | KB-3[a] | KB-V (–)[a,b] | KB-V (+)[a,b] | IC$_{50}$ [KB-V (–)]/ IC$_{50}$ [KB-V (+)] |
|---|---|---|---|---|
| Pervilleine A | 24 | >34 | 0.36 | >95 |
| Pervilleine B | >35 | 15 | 0.17 | 88 |
| Pervilleine C | 3.7 | 15 | 0.17 | 88 |
| Verapamil | 37 | 44 | 0.79 | 56 |

[a]Results are expressed as IC$_{50}$ values (concentration required to inhibit cell growth by 50%) in μM. Results are the means of the two independent experiments, with each concentration tested in triplicate.
[b]Incubations were performed in the presence (+) (1 μg/ml) or absence (–) of vinblastine.

In vivo evaluations then were performed with pervilleines B and C. In preliminary growth assays, a dose 250 μg/kg of vinblastine inhibited the growth of KB-3 cells (FIG. 6A) without significantly influencing the growth of KB-V1 cells (less than 7.4% growth inhibition) (FIG. 6B). None of these cell types was sensitive to pervilleine B (77.6 mg/kg), pervilleine C (81.2 mg/kg), or verapamil (61.4 mg/kg), at a dose of 0.136 mmol/kg (less than 8.5% growth inhibition) (FIG. 6B). However, when vinblastine was coadministered with pervilleine B or C, or verapamil, a significant growth inhibitory effect (P<0.0001) was observed with KB-V1 (FIG. 1B) implanted at the i.p. site. As summarized in Table 9, when pervilleine B, pervilleine C, or vinblastine was administered as single agents, growth inhibitory effects of 2.0, 8.5, or 0%, respectively, were observed, but when given together, inhibitory effects of 66.9, 77.7, or 60.3% resulted. In each case, relative to percent inhibition which was calculated as a summation of inhibition noted when the agents were administered singly, enhancements were observed when the agents were coadministered. Thus, because observed inhibitions were greater than those calculated, all agents were effective, and pervilleine B and pervilleine C showed a stronger effect than verapamil. In studies with pervilleine A, when administered as a single agent, growth inhibition of 1% was observed, but when given together with vinblastine, an inhibitory effect of 68.6% resulted (19). Thus, relative to pervilleine A, pervilleines B and C demonstrated similar levels of reversing activity. No significant response was observed with cells implanted at the s.c. site. In all of the cases, no significant loss in mouse body weight was observed (FIGS. 6C and D), based on established criteria (28).

TABLE 9

Calculated and observed growth inhibition of KB-V1 cells implanted at i.p. and s.c. sites

| | | Growth inhibition (%)[a] | | | |
|---|---|---|---|---|---|
| | | i.p. | | s.c. | |
| Cell line tested | Reversor | Calculated inhibition[b] | Observed inhibition[c] | Calculated inhibition[b] | Observed inhibition[c] |
| KB-V1 | verapamil | 7.4 + 0 = 7.4 | 60.3 (P < 0.0001) | 3.8 + 0 = 3.8 | 7.8 (P = 0.73) |
| | pervilleine B | 7.4 + 2.0 = 9.4 | 66.8 (P < 0.0001) | 3.8 + 0 = 3.8 | 1.4 (P = 0.87) |

TABLE 9-continued

Calculated and observed growth inhibition of KB-V1 cells implanted at i.p. and s.c. sites

|  |  | Growth inhibition (%)[a] | | | |
|---|---|---|---|---|---|
|  |  | i.p. | | s.c. | |
| Cell line tested | Reversor | Calculated inhibition[b] | Observed inhibition[c] | Calculated inhibition[b] | Observed inhibition[c] |
|  | pervilleine C | 7.4 + 8.5 = 15.9 | 77.7 ($P < 0.0001$) | 3.8 + 0 = 3.8 | 0.2 ($P = 0.96$) |

[a]Fibers filled with cells were implanted into the intraperitoneal and subcutaneous compartments of host mice. The test compounds were administrated once daily by intraperitoneal injection from days 3–6 after implantation. Fibers were retrieved on day 7. The efficacy of drugs (expressed as % growth inhibition) was determined by quantifying cells using the MTT assay (n = 6). Significance (P) was evaluated using Student's t-test (calculated % inhibition versus observed %inhibition, n = 6).
[b]Calculated % inhibition is the summation of inhibition noted when vinblastine (first value) and the reversing agent (second value) were used as single agents.
[c]Observed % inhibition resulting from coadministration of agents.

Figure 2:
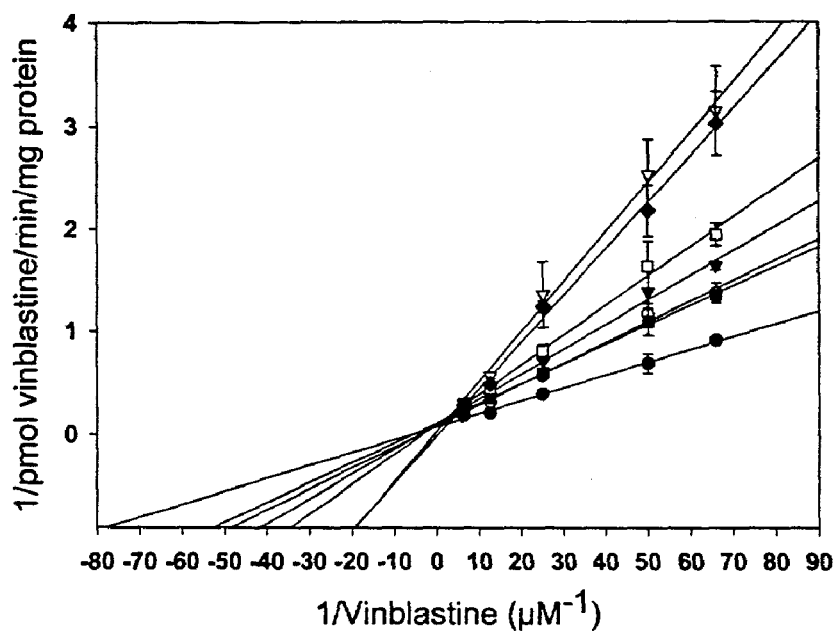
FIG. 2 contains plots of 1/pmol vinblastine/min/mg protein vs. 1/vinblastine ($\mu M^{-1}$) showing a kinetic analysis of inhibition of vinblastine accumulation.

[$^3$H]Vinblastine accumulation with KB-V1 vesicles. Inhibition of ATP-dependent vinblastine accumulation with vesicles isolated from multidrug-resistant KB-V1 cells was mediated by pervilleine A or verapamil in the 0–100 $\mu$M concentration range (FIG. 1). Accumulation was reduced from about 5.93 pmol [$^3$H]vinblastine/mg protein in control incubations to about 0.09 pmol [$^3$H]vinblastine/mg protein in the presence of pervilleine A or verapamil. Reduction was clearly dose-dependent, with inhibition of 50% being obtained at concentrations of 3.84 and 3.59 $\mu$M for pervilleine A and verapamil, respectively (FIG. 1). Using similar methodology, data were obtained from the construction of double-reciprocal plots, and competitive inhibition was observed (FIG. 2). The $K_i$ values were approximately 7.3 and 8.8 $\mu$M, for pervilleine A and verapamil, respectively.

FIG. 1 shows the dose-dependent inhibition of [$^3$H]vinblastine accumulation with KB-V1 cell membrane vesicles induced by verapamil or pervilleine A. Membrane vesicles prepared from cultured KB-V1 cells (40 $\mu$g based on protein) were incubated in buffer containing 0.16 $\mu$M [$^3$H]vinblastine and the indicated concentration of verapamil (•) or pervilleine A (○). Incubations were performed at ambient temperature for 20 minutes, and terminated using a cell harvester. Nonspecific binding was determined by the addition of a 1,000-fold excess of unlabeled vinblastine. Radioactivity was determined by liquid scintillation counting, and nonspecific binding was subtracted from all total-binding data to yield specific binding.

FIG. 2 shows a kinetic analysis of pervilleine A- or verapamil-mediated inhibition of vinblastine accumulation with KB-V1 cell membrane vesicles. Membrane vesicles were prepared from cultured KB-V1 cells and incubated in buffer containing 0.015, 0.02, 0.04, 0.08, and 0.16 $\mu$M [$^3$H]vinblastine, together with 0 (•), 5 (○), 10 (□) and 30 $\mu$M (∇) pervilleine A, or 5 (■), 10 (▼) and 30 $\mu$M (♦) verapamil. Incubations were conducted at ambient temperature for 20 minutes, and terminated using a cell harvester. Nonspecific binding was determined by performing incubations containing 1,000-fold excess of unlabeled vinblastine. Radioactivity was determined by liquid scintillation counting, and nonspecific binding was subtracted from all total-binding data to yield specific binding.

[$^3$H]Vinblastine accumulation with intact cells. Pgp-MDR cells accumulate and retain less anticancer drugs than do their drug-sensitive counterparts. Treatment of KB-3 cells with [$^3$H]vinblastine results in the accumulation of 7.1±0.17 pmol vinblastine/50×10$^4$ cells, whereas treatment of KB-V1 cells under the same experimental conditions results in the accumulation of 0.18±0.008 pmol vinblastine/50×10$^4$ cells. When KB-V1 cells were treated with verapamil or pervilleine A in the 0–40 $\mu$M range (FIG. 3), accumulation of [$^3$H]vinblastine increased from basal levels of 0.18 pmol [$^3$H]vinblastine/50×10$^4$ cells, to approximately 5 pmol [$^3$H]vinblastine/50×10$^4$ cells. The enhanced accumulation was dose-dependent, and pervilleine A appeared more effective than verapamil.

Figure 3:
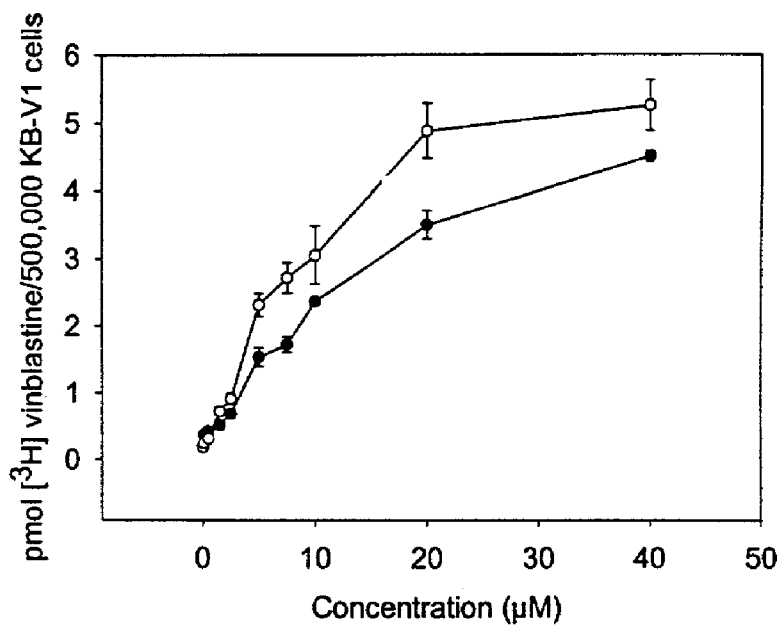
FIG. 3 contains plots of pmol [$^3$H]vinblastine/500,000 KB-VI cells vs. concentration of verapamil and pervilleine A showing increased accumulation of vinblastine.

FIG. 3 illustrates an enhanced accumulation of [$^3$H]vinblastine in KB-V1 cells as a function of added verapamil or pervilleine A (0–40 $\mu$M). Suspensions (2 ml) containing 5.0×10$^5$ KB-V1 cells in DMEM medium were placed in 24-well plates and incubated overnight in a 5% $CO_2$ incubator. [$^3$H]Vinblastine (16 nM) and the indicated concentrations of verapamil (•) or pervilleine A (○) then were added to each well. Following a one-hour incubaiton period, monolayers were washed and treated with trypsin. Cells were enumerated, and suspensions were transferred to scintillation vials for counting. The quantity of [$^3$H]vinblastine observed with blank plates containing no cells was subtracted from total binding.

RT-PCR analysis of MDR1 mRNA expression. RT-PCR studies confirmed that MDR1 mRNA gene was overexpressed in the multidrug-resistance cell lines KB-V1 and CEM/VLB$_{100}$ compared with the parental cell lines KB-3 and CEM. However, treatment of KB-V1 and CEM/VLB$_{100}$ cells for 72 hours with pervilleine A at various of concentrations ranging up to 34 $\mu$M showed no significant effect at the level of MDR1 mRNA (data not shown).

Western blot analysis of MDR1 expression. MDR1 expression with KB-3, KB-V1, CEM and CEM/VLB$_{100}$ cells was assessed using western blot analysis. As expected, MDR1 was overexpressed in multidrug-resistance cell lines KB-V1 and CEM/VLB$_{100}$ compared with parental cell lines KB-3 and CEM, but treatment of KB-V1 and CEM/VLB$_{100}$ cells for 72 hours with pervilleine A at various concentrations ranging up to 45 $\mu$M did not alter expression levels (FIG. 4).

Figure 4A:
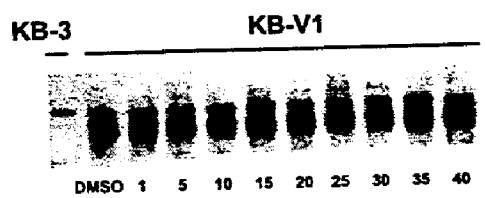
FIG. 4 contains Western blots of MDR1 expression of KB-3, KB-VI, CEM, and CEM/VLB$_{100}$ cells.
Figure 4B:
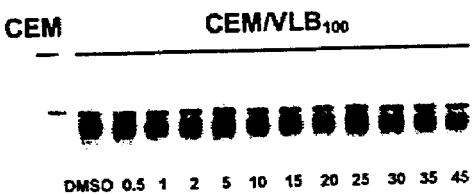

FIG. 4 contains a Western blot analysis of MDR1 expression. In FIG. 4A, KB-3 (lane 1) and KB-V1 cells (lanes 2–11) were treated with DMSO (lanes 1, 2) or 1, 5, 10, 15, 20, 25, 30, 35, and 40 $\mu$M (lanes 3–11) pervilleine A for 72 hours. In FIG. 4B, CEM (lane 1) and CEM/VLB$_{100}$ cells (lanes 2–13) were treated with DMSO (lanes 1, 2) or 0.5, 1, 2, 5, 10, 15, 20, 25, 30, 35, and 45 $\mu$M (lanes 3–13) pervilleine A for 72 hours.

Evaluation of pervilleine A in in vivo hollow fiber tests. In preliminary growth assays, it was established with hollow fibers implanted in athymic mice that a suitable concentration for KB-3, KB-V1, or KB-8-5 cells was $7.5 \times 10^5$ cells/ml. In additional preliminary studies, a dose 250 μg/kg of vinblastine inhibited the growth of KB-3 cells (FIG. 5A) without significantly influencing the growth of KB-V1 cells (less than 1% growth inhibition) (FIG. 5B). In addition to colchicine resistance, KB-8-5 cells are known to be cross-resistant with vinblastine, but to a lesser degree than KB-V1 cells (38, 39). With the in vivo hollow fiber models, treatment with 100 μg/kg of vinblastine inhibited the growth of KB-3 cells (FIG. 5A), but did not significantly influence the growth of KB-8-5 cells (less than 1.2% growth inhibition) (FIG. 5C). None of these cell types were sensitive to pervilleine A (79.2 mg/kg) or verapamil (61.4 mg/kg) at a dose of 0.136 mmol/kg (less than 5.2% growth inhibition) (FIGS. 5B and 5C). However, when vinblastine was coadministered with pervilleine A or verapamil, a significant growth inhibitory effect ($P<0.0001$) was observed with KB-V1 (FIG. 5B) or KB-8-5 cells (FIG. 5C) implanted at the i.p. site.

Figure 5:
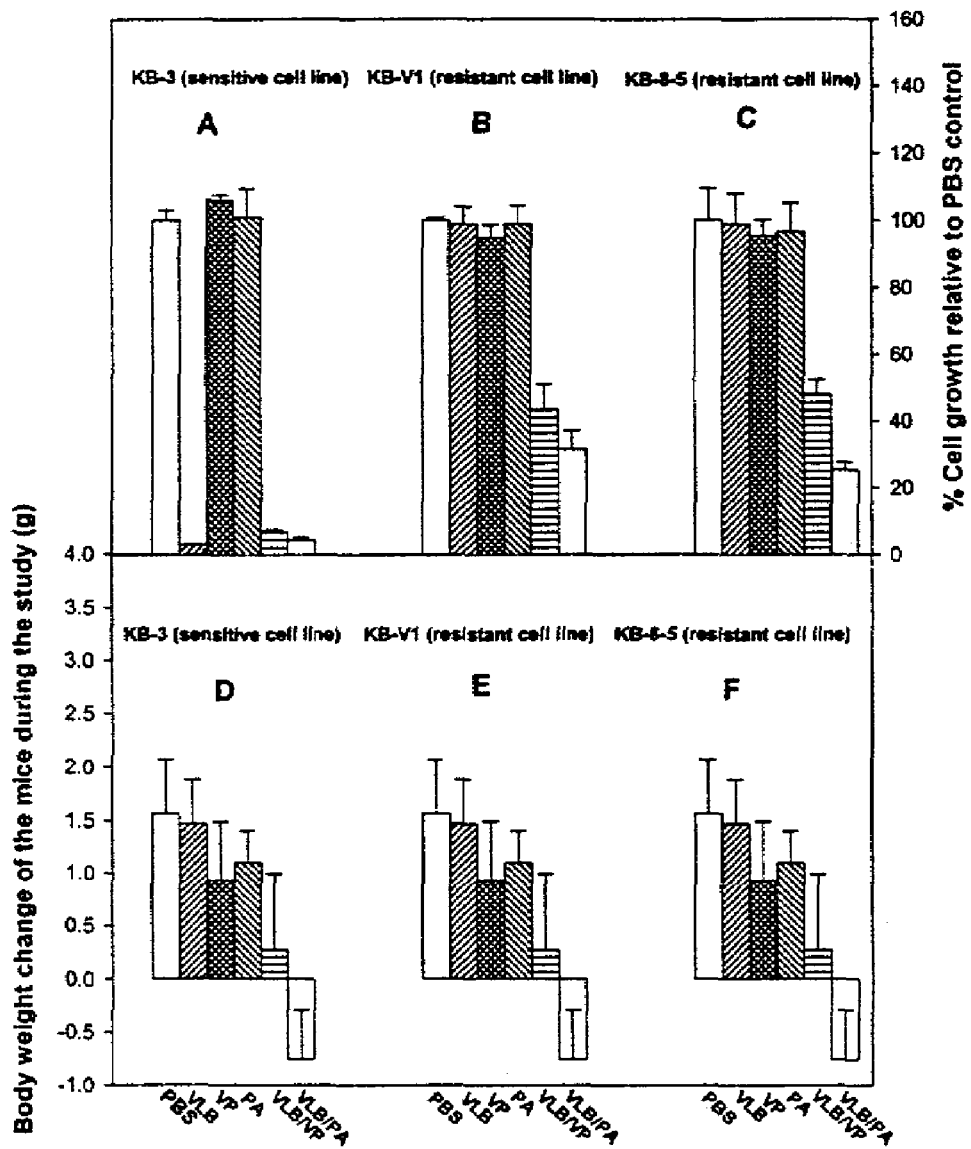
FIGS. 5 and 6 contain bar graphs summarizing the results of in vivo fiber studies showing relative % cell growth and body weight change.

FIG. 5 summarizes in vivo hollow fiber studies conducted with KB-3 (Panels A and D), KB-V1 (Panels B and E), and KB-8-5 (Panels C and F) cells implanted at the i.p. compartment of NCr nu/nu mice. Confluent monolayers of KB-3, KB-V1, and KB-8-5 cells were harvested, pelleted by centrifugation, and resuspended in conditioned medium at a concentration of $7.5 \times 10^5$ cells/ml. Fibers filled with the cells were incubated in 6-well plates overnight at 37° C. in a 5% $CO_2$ atmosphere, and then inserted into the peritoneal cavity of NCr nu/nu mice in a craniocaudal direction. The incisions were closed with skin staples. The animals were treated with PBS (control), vinblastine (VLB) (250 μg/kg: Panels A, D, B, E; 100 μg/kg: Panels C, F), verapamil (VP) (0.136 mmol/kg), pervilleine A (PA) (0.136 mmol/kg), a combination of vinblastine and verapamil (VLB/VP), or a combination of vinblastine and pervilleine A (VLB/PA) (doses of individual agents in combination regimens are the same as given above). Drugs were administrated once daily by intraperitoneal injection from day 3–6 after implantation. On day 7, mice were sacrificed and fibers were retrieved. The effectiveness of the drugs was evaluated on the basis of net growth percentage of the cells determined by MTT assays (Panels A, B, and C). Body weight was determined on day 1 and day 7 of the study, and expressed as the difference (Panels D, E, and F). The calculated % inhibitions were significantly different from the observed % inhibitions ($P<0.0001$) using Student's t-test (n=6).

Figure 6:
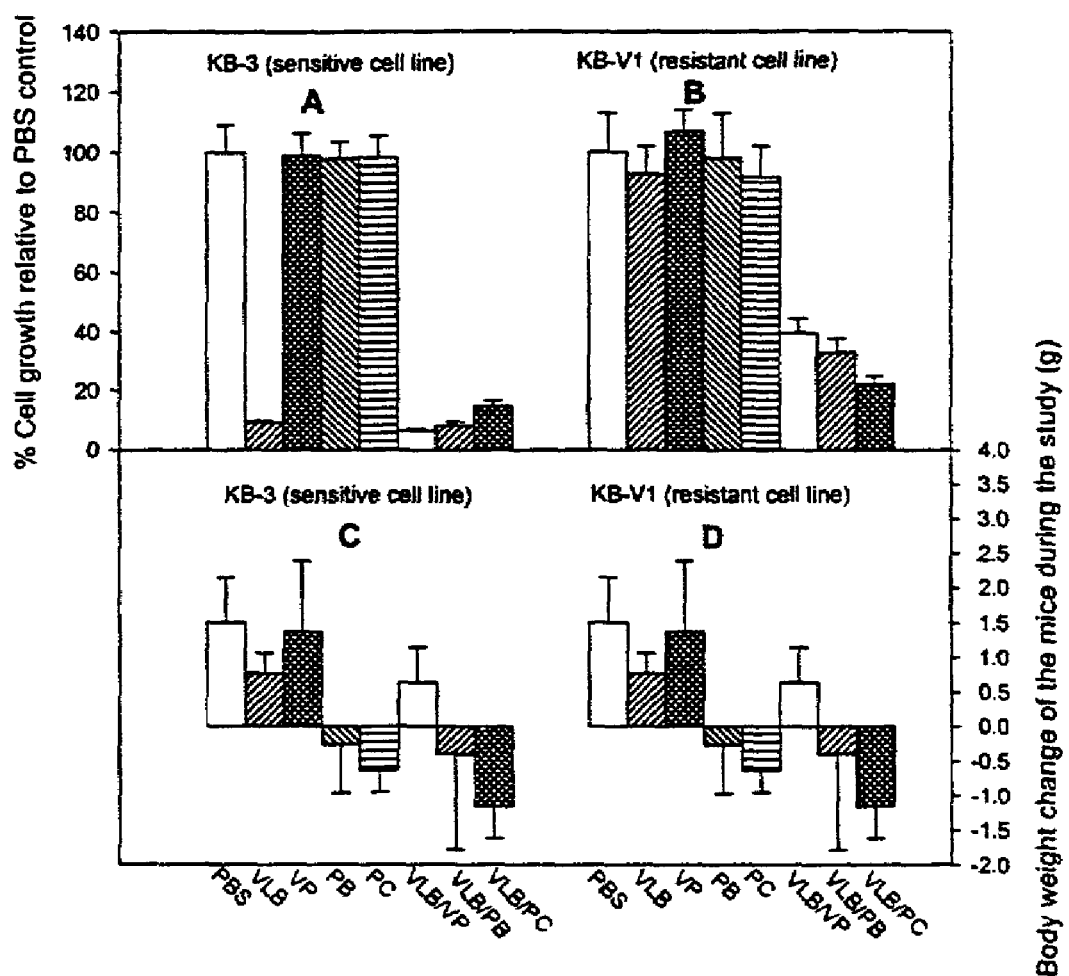

FIG. 6 illustrates in vivo hollow fiber studies conducted with KB-3 (Panels A and C) and KB-V1 (Panels B and D) cells implanted at the i.p. compartment of NCr nu/nu mice. Confluent monolayers of KB-3 and KB-V1 cells were harvested, pelleted by centrifugation, and resuspended in conditioned medium at a concentration of $5 \times 10^6$ cells/ml. Fibers filled with the cells were incubated in 6-well plates overnight at 37° C. in a 5% $CO_2$ atmosphere, then inserted into the peritoneal cavity of NCr nu/nu mice in a craniocaudal direction. The incisions were closed with skin staples. The animals were treated with PBS (control), vinblastine (VLB) (250 μg/kg), verapamil (VP) (0.136 mmol/kg), pervilleine B (PB) (0.136 mmol.kg), pervilleine C (PC) (0.136 mmol/kg), a combination of vinblastine and verapamil (VLB/VP), a combination of vinblastine and pervilleine B (VLB/PB), or a combination of vinblastine and pervilleine C (VLB/PC) (doses of individual agents in combination regimens were the same as given above). Drugs were administered once daily by intraperitoneal injection from days 3–6 after implantation. On day 7, mice were sacrificed and fibers were retrieved. The effectiveness of the drugs was evaluated on the basis of net growth percentage of the cells determined by MTT assays (Panels A and B). Body weight was determined on day 1 and day 7 of the study, and expressed as the difference (Panels C and D). The calculated % inhibitions were significantly different from the observed % inhibitions ($P<0.0001$) using Student's t-test (n=6).

The response observed with cells implanted at the s.c. site was less intense. As summarized in Table 5, when pervilleine A or vinblastine were administered as single agents, growth inhibition effects of 3.3% or 1.2%, respectively, were observed, but when given together, an inhibitory effect of 74.7% resulted. In each case, relative to percent inhibition which was calculated as a summation of inhibition noted when the agents were administered singly, enhancements were observed when the agents were coadministered. Thus, because observed inhibitions were greater than those calculated, both agents were effective, and pervilleine A showed a stronger effect than verapamil. In all cases, no significant loss in mouse body weight was observed (FIGS. 5D, 5E, and 5F), based on established criteria (28).

Cell culture has proven to be an invaluable tool for the discovery and characterization of agents capable of altering the MDR phenotype. Relative to parental KB-3 cells, KB-V1 cells are >200-fold more resistant to the growth inhibitory effect of vinblastine (6), and this as a model was employed for the discovery of various agents capable of reversing MDR (23, 24). As a result of this process, interesting natural product MDR reversing agents have been discovered (25). For example, because pervilleine A bears structural resemblance to verapamil, a well-known prototype-reversing agent, comparative studies were performed with the two compounds. In each case, the response mediated by pervilleine A was found to be equal to or greater than the response mediated by verapamil. In addition to KB-V1 cells, pervilleine A effectively reversed the MDR phenotype with KB-8-5 (Table 6) and CEM/VLB$_{100}$ cells (Table 7).

Previous studies have demonstrated that the overexpression of Pgp is a major cause for developing MDR, and decreasing expression of Pgp at either the transcriptional or protein level is one mechanism for reversing MDR (40, 41). To explore the mechanism by which pervilleine A enhances the vinblastine-sensitivity of MDR cells, the potential of pervilleine A to alter MDR1 mRNA or protein expression with KB-V1 and CEM/VLB$_{100}$ cells in culture was investigated. Treatment with various concentrations of pervilleine A for 72 hours did not significantly alter protein (FIG. 5) or mRNA expression (data not shown), and similar negative results were obtained in parallel studies conducted with verapamil (concentrations ranging up to 44 μM). With verapamil, these results are consistent with those of Hu et al. (42), who demonstrated a limited effect on MDR1 mRNA levels in KB-V1 cells after a 24-hour incubation. With CEM/VLB$_{100}$ cells, however, no inhibition of Pgp expression noted previously with verapamil was observed (40). This may be due to differences in experimental conditions, because it is known that the effect of modulators on Pgp expression might be cell line and modulator-dependent (42). In any event, it is clear that Pgp transcription and protein expression with cultured KB-V1 and CEM/VLB$_{100}$ cells were not affected by pervilleine A.

On the other hand, pervilleine A clearly altered functional aspects of Pgp. When KB-V1 cells were treated with verapamil or pervilleine A in the concentration range of 0–40 μM (FIG. 4), [$^3$H]vinblastine accumulation increased by about 27-fold (from basal levels of 0.18 pmol [$^3$H]vinblastine/ 50×10$^4$ cells, to approach 5 pmol [$^3$H]vinblastine/50×10$^4$ cells). This level of accumulation approached that of sensitive cells (7.1±0.17 pmol vinblastine/50×10$^4$ cells), indicating that restoration of the vinblastine-sensitivity of resistant cells results from enhanced intracellular accumulation of vinblastine.

Plasma membranes obtained from MDR cells bind greater quantities of anticancer drugs than their counterparts derived from drug-sensitive cells (43), and [$^3$H]vinblastine associated with plasma membrane vesicles isolated from MDR cells (23, 24, 32, 43, 44) can be used as a model to investigate the mechanism of Pgp-mediated drug transport/efflux. Treatment of membrane vesicles isolated from multidrug-resistant KB-V1 cells with pervilleine A or verapamil in the concentration range of 0–100 $\mu$M (FIG. 2) in the presence of 0.16 $\mu$M [$^3$H]vinblastine reduced [$^3$H]vinblastine accumulation by about 65-fold (from 5.93 pmol [$^3$H]vinblastine/mg protein in control incubations to about 0.09 pmol [$^3$H]vinblastine/mg protein in the presence of pervilleine A or verapamil). Thus, as is the case with verapamil, pervilleine A increased intracellular drug accumulation by inhibiting the efflux mechanism of Pgp. In order to characterize the mode of interaction, kinetic studies were performed with membrane vesicles derived from KB-V1 cells in which the effect of verapamil or pervilleine A on [$^3$H]vinblastine accumulation was determined. With both test agents, competitive inhibition was observed, suggesting interaction with the binding site normally occupied by vinblastine. In a similar manner, Cornwell et al. (44) suggested verapamil and vinblastine bind to the same site in membrane vesicles from KB-V1 cells, based on the results of vinblastine binding and vinblastine photoaffinity labeling studies. However, Pascaud et al. (45) have proposed Pgp has distinct but interacting binding sites for cytotoxic drugs (e.g., vinblastine) and reversing agents (e.g., verapamil), through analysis of the ATPase activity of Pgp. It is presently uncertain if pervilleine A action involves a unique common binding site, or two mutually exclusive, but distinct, binding sites.

Studies have been performed to define the structural or physicochemical features of reversers that might account for their effectiveness (8, 46–50). It has been suggested (48) that planar aromatic rings and nitrogen atoms are common features shared by all modulators. A $CH_2$—$CH_2$—N—$CH_2$—$CH_2$ sequence was observed (50) in most active compounds, and a methoxyphenyl moiety was found to enhance the reversing activity. The relative disposition of aromatic rings and the basic nitrogen atom are important for modulators of Pgp-associated MDR (8), suggesting a ligand-receptor relationship. Verapamil and pervilleine A bear features shared by other MDR reversers in having a tertiary nitrogen, two aromatic rings, and methoxyphenyl groups. Verapamil has three domains in common with vinblastine that appear to be important for its ability to interact with Pgp and modulate MDR (8): two aromatic rings and a basic nitrogen atom. In addition to these structural features, lipid solubility and molar refractivity might play dominant roles in reversing MDR (48). Since pervilleine A demonstrated activity in in vitro studies, the hollow fiber model was employed to further investigate in vivo potential. This is the first reported use of the hollow fiber model to assess MDR reversing agents in combination with cancer chemotherapeutic agents. In combination with vinblastine, the hollow fiber test was used to assess the capacity of verapamil or pervilleine A to effect the growth of multidrug-resistant tumor cells growing in the i.p. and s.c. compartments of mice. At pharmacologically relevant doses, the data in Table 10 indicate that both verapamil and pervilleine A are capable of reversing vinblastine sensitivity with KB-V1 and KB-8-5 cells implanted at the i.p. site (P<0.0001), which is consistent with in vitro data (Table 6). However, responses at the s.c. site were less clear (Table 10), and only pervilleine A showed a significant reversing effect (P=0.008) with KB-8-5 cells. Relative to verapamil, it is possible that pervilleine A is distributed more effectively in the rodent body.

Alternatively, with KB-8-5 cells, pervilleine A may be more effective than verapamil, in terms of reversing resistance to vinblastine. Overall, the relatively poor responses observed at the s.c. site might be due to ineffective drug delivery, or the lack of blood vessel development, since the present hollow fiber assay protocol would not enable angiogenesis (51). However, these results indicate the utility of the hollow fiber model for combination drug studies, and the promising results with pervilleine A would support more advanced testing with conventional in vivo animal models.

TABLE 10

Calculated and observed growth inhibition of KB-V1 and KB-8-5 cells implanted at i.p. and s.c. sites

| | | Growth inhibition (%)[a] | | | |
|---|---|---|---|---|---|
| | | i.p. | | s.c. | |
| Cell line tested | Reversor | Calculated inhibition[b] | Observed inhibition[c] | Calculated inhibition[b] | Observed inhibition[c] |
| KB-V1 | verapamil | 1 + 5.2 = 6.2 | 56.6 (P < 0.0001) | 0 + 10.2 = 10.8 | 13.6 (P = 0.098) |
| | pervilleine A | 1 + 1 = 2 | 68.6 (P < 0.0001) | 0 + 3.3 = 3.3 | 14.6 (P = 0.188) |
| KB-8-5 | verapamil | 1.2 + 4.7 = 5.9 | 52 (P < 0.0001) | 2.3 + 1.4 = 3.7 | 11.7 (P = 0.06) |
| | pervilleine A | 1.2 + 3.3 = 4.5 | 74.7 (P < 0.0001) | 2.3 + 2.6 = 4.9 | 28 (P = 0.008) |

[a]Fibers filled with cells were implanted into the intraperitoneal and subcutaneous compartments of host mice. The test compounds were administrated once daily by intraperitonal injection from day 3–6 after implantation. Fibers were retrieved on day 7. The efficacy of drugs (expressed as % growth inhibition) was determined by quantifying cells using the MTT assay (n = 6). Significance (P) was evaluated using Student's t-test, (calculated % inhibition versus observed %inhibition, n = 6).
[b]Calculated % inhibition is the summation of inhibition noted when vinblastine (first value) and the reversing agent (second value) were used as single agents.
[c]Observed % inhibition resulting from coadministration of agents.

Verapamil and pervilleine B or C, as well as pervilleine A, bear features shared by other MDR reversing agents, in having a tertiary nitrogen, two aromatic rings, and methoxyphenyl groups ClogP values and molar refractivity weakly correlated with potential to reverse MDR.

Because pervilleines B and C also demonstrated promising activity with in vitro studies, the hollow fiber model was employed to further investigate in vivo potential. As currently described, in combination with vinblastine, the hollow fiber test was used to assess the capacity of verapamil or pervilleines B or C to effect the growth of multidrug-resistant tumor cells growing in the i.p. and s.c. compartments of mice. At pharmacologically relevant doses, the data in Table 9 indicate both verapamil and pervilleines B or C were capable of reversing vinblastine sensitivity with KB-V1 cells implanted at the i.p. site (P<0.0001), which was consistent with in vitro data (Table 8). Poor responses were observed at the s.c. site (Table 9), possibly due to ineffective drug delivery, or the lack of blood vessel development, since the present hollow fiber assay protocol would not enable angiogenesis (51).

A primary question addressed by the current study was the in vivo activity of pervilleines A, B, and C. As demonstrated, the potential of each of these agents to activities in reverse multidrug resistance was similar. Therefore, because each of the alkaloids bear the trans-3,4-trimethoxycinnamoyl unit at the C-6 position, this may be an important structural element for activity within this compound class, and the substituents at C-3 and C-7 may play less important roles. In sum, pervilleines A, B, and C are effective inhibitors of Pgp with comparable or greater activity than verapamil.

As set forth below, administration of a multidrug resistance inhibitor of the present invention to a mammal has several potential benefits, including, for example, improving treatment using a chemotherapeutic or antibiotic drug.

The multidrug resistance inhibitors can be therapeutically administered as the neat chemical, but it is preferable to administer the inhibitors as a pharmaceutical composition or formulation. Accordingly, the present invention further provides for pharmaceutical formulations comprising, for example, a multidrug resistance inhibitor, or pharmaceutically acceptable salt or prodrug thereof, together with one or more pharmaceutically acceptable carriers and, optionally, other therapeutic and/or prophylactic ingredients. The carriers are "acceptable" in the sense of being compatible with the other ingredients of the formulation and not deleterious to the recipient thereof.

The amount of a multidrug resistance inhibitor required for use in therapy varies with the nature of the condition being treated, the length of time modulation is desired, and the age and the condition of the patient, and is ultimately determined by the attendant physician. In general, however, doses employed for adult human treatment typically are in the range of 0.001 mg/kg to about 200 mg/kg per day. A preferred dose is about 1 μg/kg to about 100 μg/kg per day. The desired dose can be conveniently administered in a single dose, or as multiple doses administered at appropriate intervals, for example as two, three, four or more subdoses per day. Multiple doses often are desired, or required, because modulation of Pgp activity can be temporary.

A "therapeutically effective" dose refers to that amount of the compound that results in achieving the desired effect. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population).

The dose ratio between toxic and therapeutic effects is the therapeutic index, which is expressed as the ratio between $LD_{50}$ and $ED_{50}$. Compounds which exhibit high therapeutic indices are preferred. The data obtained from such data can be used in formulating a range of dosage for use in humans. The dosage of such compounds preferably lies within a range of circulating concentrations that include the $ED_{50}$ with little or no toxicity. The dosage can vary within this range depending upon the dosage form employed, and the route of administration utilized.

Formulations of the present invention can be administered in a standard manner, such as orally, parenterally, sublingually, transdermally, rectally, transmucosally, topically, via inhalation, or via buccal administration. Parenteral administration includes, but is not limited to, intravenous, intraarterial, intraperitoneal, subcutaneous, intramuscular, intrathecal, and intraarticular.

For veterinary use, a multidrug resistance inhibitor, or a nontoxic salt or prodrug thereof, is administered as a suitably acceptable formulation in accordance with normal veterinary practice. The veterinarian can readily determine the dosing regimen and route of administration that is most appropriate for a particular animal.

A pharmaceutical composition containing a multidrug resistance inhibitor can be in the form of tablets or lozenges formulated in conventional manner. For example, tablets and capsules for oral administration can contain conventional excipients such as binding agents (for example, syrup, accacia, gelatin, sorbitol, tragacanth, mucilage of starch or polyvinylpyrrolidone), fillers (for example, lactose, sugar, microcrystalline cellulose, maize-starch, calcium phosphate, or sorbitol), lubricants (for example, magnesium stearate, stearic acid, talc, polyethylene glycol, or silica), disintegrants (for example, potato starch or sodium starch glycollate), or wetting agents (for example, sodium lauryl sulfate). The tablets can be coated according to methods well known in the art.

Alternatively, a multidrug resistance inhibitor can be incorporated into oral liquid preparations such as aqueous or oily suspensions, solutions, emulsions, syrups, or elixirs, for example. Moreover, formulations containing these compounds can be presented as a dry product for constitution with water or other suitable vehicle before use. Such liquid preparations can contain conventional additives, like suspending agents, such as sorbitol syrup, methyl cellulose, glucose/sugar syrup, gelatin, hydroxyethylcellulose, carboxymethyl cellulose, aluminum stearate gel, and hydrogenated edible fats; emulsifying agents, such as lecithin, sorbitan mono-oleate, or acacia; nonaqueous vehicles (which can include edible oils), such as almond oil, fractionated coconut oil, oily esters, propylene glycol, and ethyl alcohol; and preservatives, such as methyl or propyl p-hydroxybenzoate and sorbic acid.

Such preparations also can be formulated as suppositories, e.g., containing conventional suppository bases, such as cocoa butter or other glycerides. Compositions for inhalation typically can be provided in the form of a solution, suspension, or emulsion that can be administered as a dry powder or in the form of an aerosol using a conventional propellant, such as dichlorodifluoromethane or trichlorofluoromethane. Typical transdermal formulations comprise conventional aqueous or nonaqueous vehicles, such as creams, ointments, lotions, and pastes, or are in the form of a medicated plaster, patch, or membrane.

Additionally, compositions of the present invention can be formulated for parenteral administration by injection or continuous infusion. It is envisioned that injection or continuous infusion is the preferred method of administration. Formulations for injection can be in the form of suspensions, solutions, or emulsions in oily or aqueous vehicles, and can contain formulation agents, such as suspending, stabilizing, and/or dispersing agents. Alternatively, the active ingredient can be in powder form for reconstitution with a suitable vehicle (e.g., sterile, pyrogen-free water) before use.

A composition in accordance with the present invention also can be formulated as a depot preparation. Such long acting formulations can be administered by implantation (for example, subcutaneously or intramuscularly) or by intramuscular injection. Accordingly, the compounds of the invention can be formulated with suitable polymeric or hydrophobic materials (as an emulsion in an acceptable oil, for example), ion exchange resins, or as sparingly soluble derivatives (as a sparingly soluble salt, for example).

A multidrug resistance inhibitor also can be used in combination with other therapeutic agents which can be useful in the treatment of cancer and other conditions or disease states. The invention thus provides, in another aspect, a combination of a therapeutic, multidrug resistance inhibitor together with a second therapeutically active agent.

A multidrug resistance inhibitor, can be used in the preparation of a medicament for coadministration with the second therapeutically active agent in treatment of conditions where modulation of Pgp activity is beneficial. In addition, a multidrug resistance inhibitor can be used in the preparation of a medicament for use as adjunctive therapy with a second therapeutically active compound to treat such conditions. Appropriate doses of known second therapeutic agents for use in combination with a multidrug resistance inhibitor are readily appreciated by those skilled in the art.

For example, a therapeutic, multidrug resistance inhibitor can be used in combination with a cancer therapy, such as chemotherapy. In particular, a multidrug resistance inhibitor can be used in conjunction with chemotherapeutic drugs, such as cis-platin, doxorubicin, Vinca alkaloids, taxol, cyclophosphamide, ifosphamide, chlorambucil, busulfan, mechlorethamine, mitomycin, dacarbazine, carboplatin, thiotepa, daunorubicin, idarubicin, mitoxanthrone, bleomycin, esperamicin $A_1$, plicamycin, carmustine, lomustine, tauromustine, streptozocin, melphalan, dactinomycin, topotecan, adriamycin, camptothecin, interferon (alpha, beta, gamma), interleukin 2, irinotecan, docetaxel, and procarbazine, and therapeutically effective analogs, prodrugs, and derivatives thereof, for example. A multidrug resistance inhibitor also can be used in combination with drugs used to treat a condition caused by a pathogen, virus, parasite, or other microbiological vector, for example, an antiinfective, like an antibiotic.

Additional chemotherapeutic agents that can be used with a present multidrug resistance inhibitor include, but are not limited to, alkylating agents, antimetabolites, hormones and antagonists thereof, radioisotopes, antibodies, as well as natural products, and combinations thereof. For example, a multidrug resistance inhibitor of the present invention can be administered with antibiotics, such as doxorubicin and other anthracycline analogs, nitrogen mustards, such as cyclophosphamide, pyrimidine analogs such as 5-fluorouracil, cisplatin, hydroxyurea, taxol and its natural and synthetic derivatives, and the like. As another example, the inhibitor can be administered in conjunction with leuprolide or goserelin (synthetic peptide analogs of LH-RH). Examples of chemotherapeutic agents useful for the method of the present invention are listed in the following table.

| Alkylating agents | Epipodophylotoxins | Hormones and |
| --- | --- | --- |
| Nitrogen mustards | etoposide | antagonists |
| mechlorethamine | teniposide | Adrenocorticosteroids/ |
| cyclophosphamide | Antibiotics | antagonists |
| ifosfamide | actimomycin D | prednisone and |
| melphalan | daunomycin | equivalents |
| chlorambucil | (rubidomycin) | dexamethasone |
| Nitrosoureas | doxorubicin | ainoglutethimide |
| carmustine (BCNU) | (adriamycin) | Progestins |
| lomustine (CCNU) | mitoxantroneidarubicin | hydroxyprogesterone |
| semustine | bleomycinsplicamycin | caproate |
| (methyl-CCNU) | (mithramycin) | medroxyprogesterone |
| Ethylenimine/ | mitomycinC | acetate |
| Methylmelamine | dactinomycin | megestrol acetate |
| thriethylenemelamine | Enzymes | Estrogens |
| (TEM) | L-asparaginase | diethylstilbestrol |
| triethylene | Biological response | ethynyl estradiol/ |
| thiophosphoramide | modifiers | equivalents |
| (thiotepa) | interferon-alpha | Antiestrogen |
| hexamethylmelamine | IL-2 | tamoxifen |
| (HMM, altretamine) | G-CSF | Androgens |
| Alkyl sulfonates | GM-CSF | testosterone propionate |
| busulfan | Differentiation Agents | fluoxymesterone/ |
| Triazines | retinoic acid | equivalents |
| dacarbazine (DTIC) | derivatives | Antiandrogens |
| Antimetabolites | Radiosensitizers | flutamide |
| Folic Acid analogs | metronidazole | gonadotropin-releasing |
| methotrexate | misonidazole | hormone analogs |
| trimetrexate | desmethylmisonidazole | leuprolide |
| Pyrimidine analogs | pimonidazole | Nonsteroidal |
| 5-fluorouracil | etanidazole | antiandrogens |
| fluorodeoxyuridine | nimorazole | flutamide |
| gemcitabine | RSU 1069 | Photosensitizers |
| cytosine arabinoside | EO9 | hematoporphyrin |
| (AraC, cytarabine) | RB 6145 | derivatives |
| 5-azacytidine | SR4233 | Photofrin ® |
| 2,2'-difluorodeoxy- | nicotinamide | benzoporphyrin |
| cytidine | 5-bromodeozyuridine | derivatives |
| Purine analogs | 5-iododeoxyuridine | Npe6 |
| 6-mercaptopurine | bromodeoxycytidine | tin etioporphyrin |
| 6-thioguanine | Miscellaneous agents | (SnET2) |
| azathioprine | Platinium coordination | pheoboride-a |
| 2'-deoxycoformycin | complexes | bacteriochlorophyl |
| (pentostatin) | cisplatin | l-a |
| erythrohydroxynonyl- | carboplatin | naphthalocyanines |
| adenine (EHNA) | Anthracenedione | phthalocyanines |
| fludarabine phosphate | mitoxantrone | zinc |
| 2-chlorodeoxy- | Substituted urea | phthalocyanines |
| adenosine | hydroxyurea | |
| (cladribine, 2-CdA) | Methylhydrazine | |
| Type I Topoisomerase | derivatives | |
| Inhibitors | N-methylhydrazine | |
| camptothecin | (MIH) | |
| topotecan | procarbazine | |
| irinotecan | Adrenocortical | |
| Natural products | suppressant | |
| Antimitotic drugs | mitotane (o,p'-DDD) | |
| paclitaxel | ainoglutethimide | |
| Vinca alkaloids | Cytokines | |
| vinblastine (VLB) | interferon (α, β, γ) | |
| vincristine | interleukin-2 | |
| vinorelbine | | |
| Taxotere ® | | |
| (docetaxel) | | |

The multidrug resistance inhibitor also can be used in conjunction with an antiinfective agent. An antiinfective agent is a drug used to treat an individual suffering from a disease or condition caused by a bacteria, virus, parasite, or other microbiological or microscopic vector.

Antibiotic agents that can be used include, but are not limited to, sulfonamides, such as sulfacetamide sodium, sulfacycline, sulfadiazine, sulfabenzamide, sulfadoxine, sulfamerazine, sulfamethazine, sulfmethizole, sulfamethoxazole, sulfanilamide, sulfapyridine, sulfasalazine, and sulfisoxazole; a penicillin, such as penicillin G, penicillin V, cloxacillin, dicloxacillin, methicillin, nafcillin, oxacillin, amoxacillin, ampicillin, bacampicillin, cyclacillin, carbenicillin, indanylcarbenicillin, melocillin, piperacillin, and ticarcillin; a cephalosporin, such as cefadroxil, cefazolin, cephalexin, cephalothin, cephapirin, cephradine, cefaclor, cefamandole, cefmetazole, cefonicid, ceforanid, cefotetan, cefoxitin, cefpodoxime, cefprozil, cefuroxine, loracef, cefixime, cefoperazone, cefataxime, ceftazidime, ceftizoxime, ceftriaxone, or moxalactam; an aminoglycoside, such as amikacin sulfate, gentamicin sulfate, kanamycin sulfate, neomycin sulfate, nefilmican sulfate, streptomycin sulfate, and tobramycin; a macrolide, such as azithromycin, clarithromycin, erythromycin, spiramycin, and troleandomycin; a polypeptide, such as bacitracin, capreomycin sulfate, colistimethate sodium, colistin sulfate, polymyxin B sulfate, and vanomycin; a tetracycline, such as chlorotetracycline hydrochloride, demeclocycline hydrochloride, doxycycline, minocycline, oxytetracycline, and tetracycline; a fluoroquinolone, such as ciprofloxacin hydrochloride, enoxacin, lomefloxacin hydrochloride, norfloxacin, and ofloxacin; and miscellaneous antibiotics, such as chloramphenicol, clindamycin, cycloserine, fusidate sodium, ritampin, spectinomycin hydrochloride, cinoxacin, clofazimine, dapsone, ethambutal hydrochloride, isoniazid, nitrofurantoin, pyrazinamide, rifabutin, and trimethoprim. Addition classes of antibacterials include antimalarial and antifungal drugs. Antiviral drugs, such as acyclovir, cytarabine, didanosine, foscarnet, genciclovir, idoxuridine, an interferon, methisazone, rifampin, suramin, vidarabine, zalcitabine, and zidovudine, also can be used. Other antiinfective agents known to persons skilled in the art, and salts, derivatives, and prodrugs of antiinfective agents also can be used.

The combination referred to above can be presented for use in the form of a single pharmaceutical formulation, and, thus, pharmaceutical compositions comprising a combination as defined above together with a pharmaceutically acceptable diluent or carrier comprise a further aspect of the invention.

The individual components of such a combination referred to above, therefore, can be administered either sequentially or simultaneously from the same or separate pharmaceutical formulations. As is the case for the multidrug transporter modulator, a second therapeutic agent can be administered by any suitable route, for example, by oral, buccal, inhalation, sublingual, rectal, vaginal, transurethral, nasal, topical, percutaneous (i.e., transdermal), or parenteral (including intravenous, intramuscular, subcutaneous, and intracoronary) administration.

In some embodiments, a multidrug resistance inhibitor, and the second therapeutic agent are administered by the same route, either from the same or from different pharmaceutical compositions. However, in other embodiments, using the same route of administration for the therapeutic multidrug resistance inhibitor and the second therapeutic agent either is impossible or is not preferred. Persons skilled in the art are aware of the best modes of administration for each therapeutic agent, either alone or in a combination.

Obviously, many modifications and variations of the invention as hereinbefore set forth can be made without departing from the spirit and scope thereof and, therefore, only such limitations should be imposed as are indicated by the appended claims.

REFERENCES (1) M. M. Gottesman et al., *Ann. Rev. Biochem.*, 62: 385–427, (1993).
(2) M. Horio et al., *Biochem. Biophys. Acta*, 1061:106–110, (1991).
(3) W. V. D. Vire et al., *Crit. Rev. Clin. Lab. Sci.*, 35:1–57, (1998).
(4) A. H. Dantzig et al., *Cancer Res.*, 56:4171–4179, (1996).
(5) J. M. Ford et al., *Pharmacol. Rev.*, 42: 155–199, (1990).
(6) T. Watanabe et al., *Acta Oncol.*, 34: 235–241, (1995).
(7) H. L. Pearce et al., *Proc. Natl. Acad. Sci. USA*, 86:5128–5132, (1989).
(8) H. Echizen et al., *Am. Heart J.*, 109:210–217, (1985).
(9) M. Naito et al., *Cancer Chemother. Pharmacol.*, 40:S20–S24, (1997).
(10) F. Bichat et al., *Biochem. Pharmacol.*, 56:497–502, (1998).
(11) F. Hyafil et al., *Cancer Res.*, 53: 4595–4602, (1993).
(12) T. Tsuruo et al., *Cancer Res.*, 43: 2905–2910, (1983).
(13) T. Tsuruo et al., *Cancer Treat. Rep.*, 69:523–525, (1985).
(14) H. Shinoda et al., *Cancer Res.*, 49: 1722–1726, (1989).
(15) A. Kiue et al., *Br. J. Cancer*, 64:221–226, (1991).
(16) L. Kraus-Berthier et al., *Acta Oncol.*, 33:631–637, (1994).
(17) W. T. Bellamy et al., *Cancer Invest.*, 8:547–562, (1990).
(18) G. D. Pennock et al., *J. Natl. Cancer Inst.*, 83:105–110, (1991).
(19) P. Sonneveld et al., *Curr. Opin. Oncol.*, 9:543–548, (1997).
(20) K. Ueda et al., *Anti-Cancer Drug Des.*, 14:115–121, (1999).
(21) B. I. Sikic, *Oncology 5A*, 183–187, (1999).
(22) M. J. Newman et al., *Cancer Res.*, 2964–72, (2000).
(23) M. You et al., *J. Nat. Prod.*, 57:1517–1522, (1994).
(24) M. You et al., *J. Nat. Prod.*, 58:598–604, (1995).
(25) G. L. Silva et al., *J. Nat. Prod.*, 64, pp. 1514–1520 (2001.)
(26) M. Hollingshead et al., *Proc. Am. Assoc. Cancer Res.*, 34:429, (1993).
(27) J. J. Casciari et al., *J. Natl. Cancer Inst.*, 86:1846–1852, (1994).
(28) M. G. Hollingshead et al., *Life Sci.*, 57:131–141, (1995).
(29) W. T. Beck et al., *Cancer Res.*, 39:2070–2079, (1979).
(30) W. T. Beck et al., *Cancer Res.*, 46:778–784, (1986).
(31) M. M. Cornwell et al., *J. Biol. Chem.*, 281:7921–7928, (1986).
(32) A. Somanabandhu et al., *J. Nat. Prod.*, 56:233–239, (1993).
(33) L. L. Song et al., *Cancer Res.*, 59: 578–585, (1999).
(34) A. Fojo et al., *Cancer Res.*, 45:3002–7, (1985).
(35) L. Wu et al., *Cancer Res.*, 52: 3029–3034, (1992).
(36) V. Gekeler et al., *Biochem. Biophys. Res. Commun.*, 206:119–126, (1995).
(37) D. P. Wailer et al., *Contraception*, 22:183–187, (1980).
(38) D. Shen et al., *J. Biol. Chem.*, 261:7762–7770, (1986).
(39) K. N. Thimmariah et al., *Oncol. Res.*, 10:29–41, (1998).
(40) C. Muller et al., *Int. J. Cancer*, 56:749–754, (1994).
(41) K. E. Sampson et al., *Cancer Lett.*, 68:7–14, (1993).
(42) Y. P. Hu et al., *Anti-Cancer Drugs*, 7:738–744, (1996).
(43) W. T. Beck, In: Roninson, I. B. (eds.), Drug Accumulation and Binding in P-Glycoprotein-Associated Multidrug Resistance, pp. 215–227.
New York: Plenum Publishing Corp., 1991.

(44) M. M. Cornwell et al., *J. Biol. Chem.*, 262:2166–2170, (1987).
(45) C. Pascaud et al., *Biochem. J.*, 333:351–358, (1998).
(46) W. D. Stein, *Physiol. Rev.*, 77:545–590, (1997).
(47) G. Klopman et al., *Mol. Pharmacol.*, 52:323–334, (1997).
(48) J. M. Zamora et al., *Mol. Pharmacol.*, 33:454–462, (1988).
(49) J. L. Weaver et al., *Int. J. Cancer*, 54:456–461, (1993).
(50) G. Klopman et al., *Cancer Res.*, 52:4121–4129, (1992).
(51) R. M. Phillipes et al., *Cancer Res.*, 58:5263–5266, (1998).
(52) T. Plowman, In: *Ethnobotany in the Neotropics;* Prance G. T.; Kallunki, J. A., Eds.; New York Botanical Garden: Bronx, N.Y., 1984; vol. 1, pp 62–111.
(53) M. S. Al-Said et al., *Phytochemistry*, 25, 851–853 (1986).
(54) C. G. Chaves et al., C. G.; Schapoval, E. E. S.; Zuanazzi, J. A.; Diehl, E.; de Siqueira, N. C. S.; Henriques, A. T. *Erythroxylum argentinum:* Assays for Anti-inflammatory Activity. *J. Ethnopharmacol.*, 22, 117–120 (1988).
(55) C. N. Tomesi et al., *Fitoterapia*, 57, 46–50 (1986).
(56) K. Doerk-Schmitz et al., *Phytochemisty*, 35, 107–110 (1994).
(57) G. Fodor et al. *Nat. Prod. Rep.*, 11, 443–450 (1994).
(58) R. Glaser et al., *J. Org. Chem.*, 53, 2172–2180 (1988).
(59) M. S. Al-Said et al., *J. Chem. Soc., Perkin Trans.*, 1, 957–959 (1986).
(60) J. T. Agar et al., *J. Chem. Soc., Perkin Trans.*, 1, 1550–1553 (1976).
(61) A. L. Payo-Hill al., *Phytochemistry*, 54, 927–932 (2000).
(62) M. Lounasmaa, In: *The Alkaloids. Chemistry and Pharmacology;* Brossi, A., Ed.; Academic Press, Inc.: New York, vol. 33, pp 1–81 (1988).
(63) Y. M. El-Iman et al., *Phytochemistry*, 26, 2385–2389 (1987).
(64) T. A. Broadbent et al., *Heterocycles*, 20, 863–980 (1983).
(65) G. A. Cordell et al., *Tetrahedron*, 47, 3521–3534 (1991).
(66) E. Wenkert et al., *Acc. Chem. Res.*, 7, 46–51 (1974).
(67) C. S. Huber et al., *Can. J. Chem.*, 49, 3258–3271 (1971).
(68) K. Likhitwitayawuid et al., *J. Nat. Prod.*, 56, 30–38 (1993).
(69) W. R. Wilson et al., *Br. J. Cancer*, 74, S43–S47 (1996).
(70) H. H. Lee et al., *Anti-cancer Drug Design*, 14, 487–497 (1999).
(71) F. Hyafil et al., *Cancer Res.*, 53, 4595–4602 (1993).
(72) M. E. Wall et al., *J. Med. Chem.*, 37, 1465–1470 (1994).
(73) F. J. Sharom et al., *Biochem. Pharmacol.*, 58, 571–586 (1999).
(74) M. N. Prichard et al., *Antiviral Res.*, 14, 181–206 (1990).
(75) Q. Mi et al., *Cancer Res.*, 61, pp. 4030–4037 (2001).
(76) G. Sheldrick, M.SHELXTL for IRIS, Vers. 5.03 (Copyright 1990–1995), SAXI, Siemens Analytical X-ray Instrument, Inc., Madison, Wis.
(77) Crystallographic data for tropane-3α,6β,7β-triol 3-phenylacetate (1) have been deposited at the Cambridge Crystallographic Data Center. Copies of the data can be obtained, free of charge, on application to the Director, CCDC, 12 Union Road, Cambridge CB2 1EZ, UK (Fax: +44-(0)1223-336033 or e-mail: deposit@ccdc.cam.ac.uk).

What is claimed is:

1. A compound selected from the group consisting of:

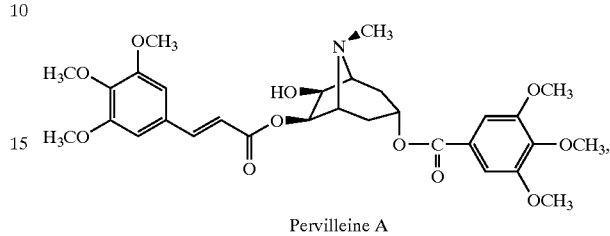

Pervilleine A

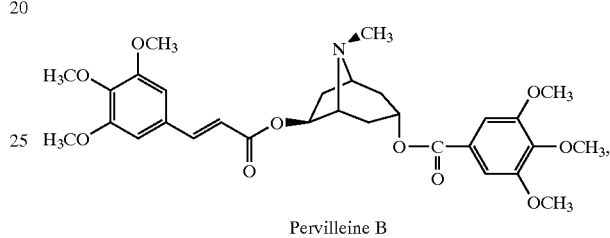

Pervilleine B

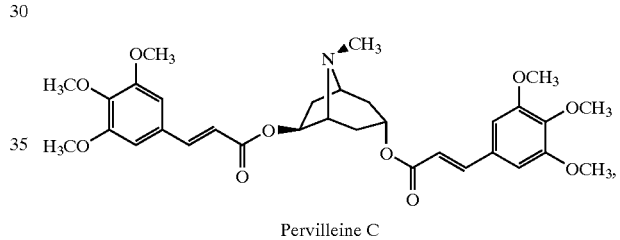

Pervilleine C

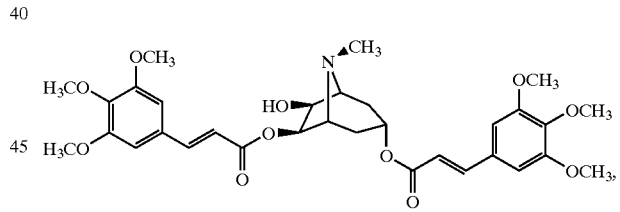

Pervilleine D

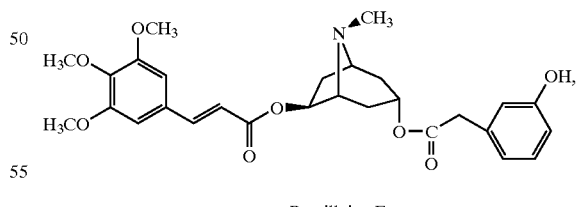

Pervilleine E

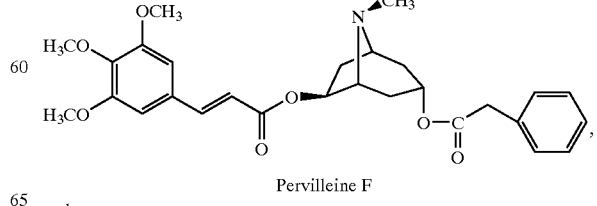

Pervilleine F and

-continued

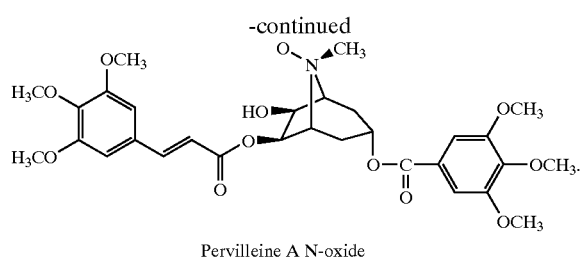

Pervilleine A N-oxide

2. The compound of claim 1 wherein the compound is selected from the group consisting of pervilleine A, pervilleine B, and pervilleine C.

3. A composition comprising
   (a) an active compund selected from the group consisting of pervilleine A, pervilleine B, pervilleine C, pervilleine D, pervilleine E, pervilleine F, pervilleine A N-oxide, and mixtures thereof; and
   (b) a pharmaceutically acceptable carrier.

* * * * *

UNITED STATES PATENT AND TRADEMARK OFFICE
CERTIFICATE OF CORRECTION

PATENT NO. : 6,989,396 B2
DATED : January 24, 2006
INVENTOR(S) : Kinghorn et al.

It is certified that error appears in the above-identified patent and that said Letters Patent is hereby corrected as shown below:

<u>Column 1,</u>
Lines 13-15, insert -- This invention was made with Government support under contract CA 52956 awarded by the National Institutes of Health. The Government has certain rights in this invention. --.

Signed and Sealed this

Fourth Day of April, 2006

JON W. DUDAS
*Director of the United States Patent and Trademark Office*

UNITED STATES PATENT AND TRADEMARK OFFICE
CERTIFICATE OF CORRECTION

PATENT NO. : 6,989,396 B2  Page 1 of 1
APPLICATION NO. : 10/119874
DATED : January 24, 2006
INVENTOR(S) : Kinghorn et al.

It is certified that error appears in the above-identified patent and that said Letters Patent is hereby corrected as shown below:

Column 44, line 6, "compund" should be -- compound --

Signed and Sealed this

Sixth Day of November, 2007

JON W. DUDAS
*Director of the United States Patent and Trademark Office*